US011261471B2

(12) United States Patent
Rome et al.

(10) Patent No.: US 11,261,471 B2
(45) Date of Patent: Mar. 1, 2022

(54) METHODS AND COMPOSITIONS FOR MAKING VAULT PARTICLES IN YEAST

(71) Applicants: The Regents of the University of California, Oakland, CA (US); Vault Pharma Inc., Los Angeles, CA (US)

(72) Inventors: Leonard H. Rome, Tarzana, CA (US); Shaily Mahendra, Santa Monica, CA (US); Meng Wang, Los Angeles, CA (US); Valerie A. Kickhoefer, Sherman Oaks, CA (US); Oliver Karl Foellmer, Santa Monica, CA (US)

(73) Assignees: The Regents of the University of California, Oakland, CA (US); Vault Pharma Inc., Los Angeles, CA (US)

( * ) Notice: Subject to any disclaimer, the term of this patent is extended or adjusted under 35 U.S.C. 154(b) by 50 days.

(21) Appl. No.: 16/414,465

(22) Filed: May 16, 2019

(65) Prior Publication Data
US 2019/0352689 A1 Nov. 21, 2019

Related U.S. Application Data

(60) Provisional application No. 62/673,240, filed on May 18, 2018.

(51) Int. Cl.
| | | |
|---|---|---|
| *C12P 21/02* | (2006.01) |
| *C07K 14/47* | (2006.01) |
| *A61K 47/42* | (2017.01) |
| *B82Y 5/00* | (2011.01) |
| *A61J 3/00* | (2006.01) |
| *A61K 47/00* | (2006.01) |

(52) U.S. Cl.
CPC .............. *C12P 21/02* (2013.01); *A61J 3/00* (2013.01); *A61K 47/00* (2013.01); *A61K 47/42* (2013.01); *B82Y 5/00* (2013.01); *C07K 14/47* (2013.01); *C07K 2319/00* (2013.01)

(58) Field of Classification Search
CPC .................................................. C12P 21/02

USPC ........................................................ 435/69.1
See application file for complete search history.

(56) References Cited

U.S. PATENT DOCUMENTS

| 8,933,203 B2 * | 1/2015 | Rome .................... A61K 47/42 |
| | | 530/402 |
| 9,181,312 B2 | 11/2015 | Rome et al. |
| 2017/0246119 A1 | 8/2017 | Mrazek |

OTHER PUBLICATIONS

Yu et al., PTEN Associates with the Vault Particles in HeLa Cells. J. of Biol Chem vol. 277, No. 43, Issue of Oct. 25, pp. 40247-40252, 2002.*
Sinclair et al., Synonymous codon usage bias and the expression of human glucocerebrosidase in the methylotrophic yeast, Pichia pastoris. Protein Expression and Purification 26 (2002) 96-105.*
Margiotta et al., "Expression of the Major Vault Protein (MVP) and Cellular Vault Particles in Fish", Jul. 15, 2017, pp. 1981-1992, vol. 300, No. 11, Publisher: Anat Rec (Hoboken).
International Search Report received in PCT/US2019/032685 dated Aug. 28, 2019.
Written Opinion received in PCT/US2019/032685 dated Aug. 28, 2019.
Wang et al., "Synthesis and assembly of human vault particles in yeast", Sep. 25, 2018, pp. 2941-2950, vol. 115, No. 12, Publisher: Biotechnol Bioeng.
Yu, et al., "Modulation of the Vault Protein-Protein Interaction for Tuning of Molecular Release", Nov. 1, 2017, p. 14816, vol. 7, No. 1, Publisher: Sci Rep.
Zheng, et al., "Characterization of MVP and VPARP assembly into vault ribonucleoprotein complexes", Jan. 7, 2005, pp. 100-107, vol. 326, No. 1, Publisher: Biochem Biophys Res Commun.

* cited by examiner

*Primary Examiner* — Sheridan Swope
(74) *Attorney, Agent, or Firm* — Suzannah K. Sundby, Esq.; Canady + Lortz LLP

(57) ABSTRACT

Disclosed herein are methods and compositions for making vault particles in yeast hosts and yeast vaults produced therefrom.

21 Claims, 9 Drawing Sheets

Specification includes a Sequence Listing.

SEQUENCE LISTING

<160> NUMBER OF SEQ ID NOS: 2

<210> SEQ ID NO 1
<211> LENGTH: 2679
<212> TYPE: DNA

```
<213> ORGANISM: Artificial Sequence
<220> FEATURE:
<223> OTHER INFORMATION: Codon-optimized sequence encoding human MVP
<220> FEATURE:
<221> NAME/KEY: CDS
<222> LOCATION: (1)..(2679)

<400> SEQUENCE: 1 atg gca aca gag gag ttt att atc aga atc cca cct tat cac tat atc      48
Met Ala Thr Glu Glu Phe Ile Ile Arg Ile Pro Pro Tyr His Tyr Ile
1               5                   10                  15 cac gtt ttg gac cag aac agt aat gtc tca aga gtc gaa gtt ggt cca      96
His Val Leu Asp Gln Asn Ser Asn Val Ser Arg Val Glu Val Gly Pro
                20                  25                  30 aag act tac atc aga caa gat aac gaa aga gtt ttg ttc gct cct atg     144
Lys Thr Tyr Ile Arg Gln Asp Asn Glu Arg Val Leu Phe Ala Pro Met
            35                  40                  45 aga atg gtt act gtt cca cct aga cat tat tgt act gtt gct aat cca     192
Arg Met Val Thr Val Pro Pro Arg His Tyr Cys Thr Val Ala Asn Pro
        50                  55                  60 gtt tcc aga gat gct caa ggt ttg gtt ttg ttt gat gtt act ggt caa     240
Val Ser Arg Asp Ala Gln Gly Leu Val Leu Phe Asp Val Thr Gly Gln
65                  70                  75                  80 gtt aga ttg aga cac gct gat ttg gaa att aga ttg gct caa gat cca     288
Val Arg Leu Arg His Ala Asp Leu Glu Ile Arg Leu Ala Gln Asp Pro
                85                  90                  95 ttc cct ttg tac cct ggt gaa gtt ttg gaa aag gat att act cca ttg     336
Phe Pro Leu Tyr Pro Gly Glu Val Leu Glu Lys Asp Ile Thr Pro Leu
                100                 105                 110 caa gtt gtt ttg cct aac act gct ttg cat ttg aag gct ttg ttg gat     384
Gln Val Val Leu Pro Asn Thr Ala Leu His Leu Lys Ala Leu Leu Asp
            115                 120                 125 ttt gag gat aag gat gga gat aaa gtt gtt gct gga gat gag tgg ttg     432
Phe Glu Asp Lys Asp Gly Asp Lys Val Val Ala Gly Asp Glu Trp Leu
        130                 135                 140 ttc gaa ggt cca ggt act tat att cct aga aag gaa gtt gag gtt gtt     480
Phe Glu Gly Pro Gly Thr Tyr Ile Pro Arg Lys Glu Val Glu Val Val
145                 150                 155                 160 gaa atc atc caa gct act atc atc aga caa aac cag gct ttg aga ttg     528
Glu Ile Ile Gln Ala Thr Ile Ile Arg Gln Asn Gln Ala Leu Arg Leu
                165                 170                 175 aga gct aga aag gag tgt tgg gat aga gat ggt aaa gaa aga gtt act     576
Arg Ala Arg Lys Glu Cys Trp Asp Arg Asp Gly Lys Glu Arg Val Thr
            180                 185                 190 ggt gaa gag tgg ttg gtt act act gtt ggt gct tac ttg cca gct gtt     624
Gly Glu Glu Trp Leu Val Thr Thr Val Gly Ala Tyr Leu Pro Ala Val
        195                 200                 205 ttc gaa gag gtt ttg gat ttg gtt gat gct gtt att ttg act gaa aag     672
Phe Glu Glu Val Leu Asp Leu Val Asp Ala Val Ile Leu Thr Glu Lys
    210                 215                 220 act gct ttg cat ttg aga gct aga aga aac ttt aga gat ttc aga ggt     720
Thr Ala Leu His Leu Arg Ala Arg Arg Asn Phe Arg Asp Phe Arg Gly
225                 230                 235                 240 gtt tcc aga aga acc gga gag gaa tgg ttg gtt act gtt caa gat act     768
Val Ser Arg Arg Thr Gly Glu Glu Trp Leu Val Thr Val Gln Asp Thr
                245                 250                 255 gaa gct cat gtt cct gat gtt cac gaa gag gtt ttg ggt gtt gtt cca     816
Glu Ala His Val Pro Asp Val His Glu Glu Val Leu Gly Val Val Pro
            260                 265                 270 att act act ttg ggt cct cac aac tat tgt gtt att ttg gac cca gtt     864
Ile Thr Thr Leu Gly Pro His Asn Tyr Cys Val Ile Leu Asp Pro Val
```

-continued

```
                275                 280                 285
ggt cct gat ggt aaa aac caa ttg ggt caa aag aga gtt gtt aag ggt    912
Gly Pro Asp Gly Lys Asn Gln Leu Gly Gln Lys Arg Val Val Lys Gly
    290                 295                 300 gaa aag tct ttc ttt ttg caa cca ggt gaa caa ttg gaa caa ggt att    960
Glu Lys Ser Phe Phe Leu Gln Pro Gly Glu Gln Leu Glu Gln Gly Ile
305                 310                 315                 320 caa gat gtt tac gtt ttg tct gag caa caa ggt ttg ttg tta aga gct   1008
Gln Asp Val Tyr Val Leu Ser Glu Gln Gln Gly Leu Leu Leu Arg Ala
                325                 330                 335 ttg caa cct ttg gaa gag ggt gaa gat gaa gag aag gtt tct cat caa   1056
Leu Gln Pro Leu Glu Glu Gly Glu Asp Glu Glu Lys Val Ser His Gln
            340                 345                 350 gct gga gat cat tgg ttg att aga ggt cca ttg gag tat gtt cct tct   1104
Ala Gly Asp His Trp Leu Ile Arg Gly Pro Leu Glu Tyr Val Pro Ser
        355                 360                 365 gct aaa gtt gaa gtt gtt gaa gag aga caa gct att cca ttg gat gaa   1152
Ala Lys Val Glu Val Val Glu Glu Arg Gln Ala Ile Pro Leu Asp Glu
    370                 375                 380 aac gag ggt atc tac gtt caa gat gtt aag act ggt aaa gtt aga gct   1200
Asn Glu Gly Ile Tyr Val Gln Asp Val Lys Thr Gly Lys Val Arg Ala
385                 390                 395                 400 gtt att ggt tct act tat atg ttg act caa gat gag gtt ttg tgg gaa   1248
Val Ile Gly Ser Thr Tyr Met Leu Thr Gln Asp Glu Val Leu Trp Glu
                405                 410                 415 aag gag ttg cca cct ggt gtt gaa gag ttg ttg aac aag ggt caa gat   1296
Lys Glu Leu Pro Pro Gly Val Glu Glu Leu Leu Asn Lys Gly Gln Asp
            420                 425                 430 cca ttg gct gat aga ggt gaa aag gat act gct aaa tct ttg caa cca   1344
Pro Leu Ala Asp Arg Gly Glu Lys Asp Thr Ala Lys Ser Leu Gln Pro
        435                 440                 445 ttg gct cct aga aac aag act aga gtt gtt tct tac aga gtt cct cat   1392
Leu Ala Pro Arg Asn Lys Thr Arg Val Val Ser Tyr Arg Val Pro His
    450                 455                 460 aat gct gct gtt caa gtt tac gat tat aga gag aaa aga gct aga gtt   1440
Asn Ala Ala Val Gln Val Tyr Asp Tyr Arg Glu Lys Arg Ala Arg Val
465                 470                 475                 480 gtt ttt ggt cca gaa ttg gtt tct ttg ggt cct gaa gag caa ttc act   1488
Val Phe Gly Pro Glu Leu Val Ser Leu Gly Pro Glu Glu Gln Phe Thr
                485                 490                 495 gtt ttg tct ttg tct gct ggt aga cca aaa aga cca cat gct aga aga   1536
Val Leu Ser Leu Ser Ala Gly Arg Pro Lys Arg Pro His Ala Arg Arg
            500                 505                 510 gct ttg tgt ttg ttg ttg ggt cca gat ttc ttt act gat gtt atc act   1584
Ala Leu Cys Leu Leu Leu Gly Pro Asp Phe Phe Thr Asp Val Ile Thr
        515                 520                 525 atc gaa act gct gat cat gct aga ttg caa ttg caa ttg gct tat aac   1632
Ile Glu Thr Ala Asp His Ala Arg Leu Gln Leu Gln Leu Ala Tyr Asn
    530                 535                 540 tgg cac ttt gag gtt aat gat aga aaa gat cca caa gaa act gct aaa   1680
Trp His Phe Glu Val Asn Asp Arg Lys Asp Pro Gln Glu Thr Ala Lys
545                 550                 555                 560 ttg ttt tct gtt cct gat ttc gtt gga gat gct tgt aaa gct att gct   1728
Leu Phe Ser Val Pro Asp Phe Val Gly Asp Ala Cys Lys Ala Ile Ala
                565                 570                 575 tcc aga gtt aga ggt gct gtt gct tct gtt act ttc gat gat ttc cat   1776
Ser Arg Val Arg Gly Ala Val Ala Ser Val Thr Phe Asp Asp Phe His
            580                 585                 590 aag aac tct gct aga atc atc aga act gct gtt ttc ggt ttc gag act   1824
Lys Asn Ser Ala Arg Ile Ile Arg Thr Ala Val Phe Gly Phe Glu Thr
```

```
Lys Asn Ser Ala Arg Ile Ile Arg Thr Ala Val Phe Gly Phe Glu Thr
                595                 600                 605 tct gaa gct aaa ggt cca gat ggt atg gct ttg cca aga cct aga gat      1872
Ser Glu Ala Lys Gly Pro Asp Gly Met Ala Leu Pro Arg Pro Arg Asp
610                 615                 620 caa gct gtt ttc cct caa aac ggt ttg gtt gtt tct tct gtt gat gtt      1920
Gln Ala Val Phe Pro Gln Asn Gly Leu Val Val Ser Ser Val Asp Val
625                 630                 635                 640 caa tct gtt gag cca gtt gat caa aga act aga gat gct ttg caa aga      1968
Gln Ser Val Glu Pro Val Asp Gln Arg Thr Arg Asp Ala Leu Gln Arg
                645                 650                 655 tct gtt caa ttg gct atc gaa atc act act aat tct caa gag gct gct      2016
Ser Val Gln Leu Ala Ile Glu Ile Thr Thr Asn Ser Gln Glu Ala Ala
                660                 665                 670 gct aag cac gaa gct caa aga ttg gaa caa gag gct aga ggt aga ttg      2064
Ala Lys His Glu Ala Gln Arg Leu Glu Gln Glu Ala Arg Gly Arg Leu
                675                 680                 685 gaa aga caa aag att ttg gat caa tct gaa gct gag aag gct aga aaa      2112
Glu Arg Gln Lys Ile Leu Asp Gln Ser Glu Ala Glu Lys Ala Arg Lys
690                 695                 700 gag ttg ttg gaa ttg gag gct ttg tct atg gct gtt gaa tct act ggt      2160
Glu Leu Leu Glu Leu Glu Ala Leu Ser Met Ala Val Glu Ser Thr Gly
705                 710                 715                 720 act gct aag gct gaa gct gag tcc aga gct gaa gct gct aga att gaa      2208
Thr Ala Lys Ala Glu Ala Glu Ser Arg Ala Glu Ala Ala Arg Ile Glu
                725                 730                 735 gga gag ggt tct gtt ttg cag gct aag ttg aaa gct cag gct ttg gct      2256
Gly Glu Gly Ser Val Leu Gln Ala Lys Leu Lys Ala Gln Ala Leu Ala
                740                 745                 750 att gaa act gag gct gaa ttg caa aga gtt caa aaa gtt aga gag ttg      2304
Ile Glu Thr Glu Ala Glu Leu Gln Arg Val Gln Lys Val Arg Glu Leu
                755                 760                 765 gaa ttg gtt tac gct aga gcc caa ttg gag ttg gaa gtt tct aag gct      2352
Glu Leu Val Tyr Ala Arg Ala Gln Leu Glu Leu Glu Val Ser Lys Ala
770                 775                 780 caa caa ttg gct gag gtt gaa gtt aag aag ttt aag caa atg act gag      2400
Gln Gln Leu Ala Glu Val Glu Val Lys Lys Phe Lys Gln Met Thr Glu
785                 790                 795                 800 gct att ggt cca tct act att aga gat ttg gct gtt gct ggt cct gaa      2448
Ala Ile Gly Pro Ser Thr Ile Arg Asp Leu Ala Val Ala Gly Pro Glu
                805                 810                 815 atg cag gtt aag ttg ttg caa tct ttg ggt ttg aaa tct act ttg atc      2496
Met Gln Val Lys Leu Leu Gln Ser Leu Gly Leu Lys Ser Thr Leu Ile
                820                 825                 830 act gat ggt tct act cca att aac ttg ttt aat act gct ttc ggt ttg      2544
Thr Asp Gly Ser Thr Pro Ile Asn Leu Phe Asn Thr Ala Phe Gly Leu
                835                 840                 845 ttg ggt atg ggt cca gag ggt caa cct ttg ggt aga aga gtt gct tct      2592
Leu Gly Met Gly Pro Glu Gly Gln Pro Leu Gly Arg Arg Val Ala Ser
850                 855                 860 ggt cca tct cct ggt gaa ggt att tct cca cag tca gcc caa gca cct      2640
Gly Pro Ser Pro Gly Glu Gly Ile Ser Pro Gln Ser Ala Gln Ala Pro
865                 870                 875                 880 caa gca cca gga gat aat cat gtc gtt cca gtt ctt aga                  2679
Gln Ala Pro Gly Asp Asn His Val Val Pro Val Leu Arg
                885                 890

<210> SEQ ID NO 2
<211> LENGTH: 893
<212> TYPE: PRT
```

<213> ORGANISM: Artificial Sequence
<220> FEATURE:
<223> OTHER INFORMATION: Synthetic Construct

<400> SEQUENCE: 2

Met Ala Thr Glu Glu Phe Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Met
        35                  40                  45

Arg Met Val Thr Val Pro Pro Arg His Tyr Cys Thr Val Ala Asn Pro
50                  55                  60

Val Ser Arg Asp Ala Gln Gly Leu Val Leu Phe Asp Val Thr Gly Gln
65                  70                  75                  80

Val Arg Leu Arg His Ala Asp Leu Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asp Gly Asp Lys Val Val Ala Gly Asp Glu Trp Leu
130                 135                 140

Phe Glu Gly Pro Gly Thr Tyr Ile Pro Arg Lys Glu Val Glu Val Val
145                 150                 155                 160

Glu Ile Ile Gln Ala Thr Ile Ile Arg Gln Asn Gln Ala Leu Arg Leu
                165                 170                 175

Arg Ala Arg Lys Glu Cys Trp Asp Arg Asp Gly Lys Glu Arg Val Thr
            180                 185                 190

Gly Glu Glu Trp Leu Val Thr Thr Val Gly Ala Tyr Leu Pro Ala Val
        195                 200                 205

Phe Glu Glu Val Leu Asp Leu Val Asp Ala Val Ile Leu Thr Glu Lys
            210                 215                 220

Thr Ala Leu His Leu Arg Ala Arg Arg Asn Phe Arg Asp Phe Arg Gly
225                 230                 235                 240

Val Ser Arg Arg Thr Gly Glu Glu Trp Leu Val Thr Val Gln Asp Thr
                245                 250                 255

Glu Ala His Val Pro Asp Val His Glu Val Leu Gly Val Val Pro
            260                 265                 270

Ile Thr Thr Leu Gly Pro His Asn Tyr Cys Val Ile Leu Asp Pro Val
        275                 280                 285

Gly Pro Asp Gly Lys Asn Gln Leu Gly Gln Lys Arg Val Val Lys Gly
290                 295                 300

Glu Lys Ser Phe Phe Leu Gln Pro Gly Glu Gln Leu Glu Gln Gly Ile
305                 310                 315                 320

Gln Asp Val Tyr Val Leu Ser Glu Gln Gln Gly Leu Leu Leu Arg Ala
                325                 330                 335

Leu Gln Pro Leu Glu Glu Gly Glu Asp Glu Glu Lys Val Ser His Gln
            340                 345                 350

Ala Gly Asp His Trp Leu Ile Arg Gly Pro Leu Glu Tyr Val Pro Ser
        355                 360                 365

Ala Lys Val Glu Val Val Glu Glu Arg Gln Ala Ile Pro Leu Asp Glu
370                 375                 380

Asn Glu Gly Ile Tyr Val Gln Asp Val Lys Thr Gly Lys Val Arg Ala

```
385                 390                 395                 400
Val Ile Gly Ser Thr Tyr Met Leu Thr Gln Asp Glu Val Leu Trp Glu
                405                 410                 415

Lys Glu Leu Pro Pro Gly Val Glu Glu Leu Asn Lys Gly Gln Asp
                420                 425                 430

Pro Leu Ala Asp Arg Gly Glu Lys Asp Thr Ala Lys Ser Leu Gln Pro
                435                 440                 445

Leu Ala Pro Arg Asn Lys Thr Arg Val Val Ser Tyr Arg Val Pro His
450                 455                 460

Asn Ala Ala Val Gln Val Tyr Asp Tyr Arg Glu Lys Arg Ala Arg Val
465                 470                 475                 480

Val Phe Gly Pro Glu Leu Val Ser Leu Gly Pro Glu Glu Gln Phe Thr
                485                 490                 495

Val Leu Ser Leu Ser Ala Gly Arg Pro Lys Arg Pro His Ala Arg Arg
                500                 505                 510

Ala Leu Cys Leu Leu Leu Gly Pro Asp Phe Phe Thr Asp Val Ile Thr
                515                 520                 525

Ile Glu Thr Ala Asp His Ala Arg Leu Gln Leu Gln Leu Ala Tyr Asn
                530                 535                 540

Trp His Phe Glu Val Asn Asp Arg Lys Asp Pro Gln Glu Thr Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
                580                 585                 590

Lys Asn Ser Ala Arg Ile Ile Arg Thr Ala Val Phe Gly Phe Glu Thr
                595                 600                 605

Ser Glu Ala Lys Gly Pro Asp Gly Met Ala Leu Pro Arg Pro Arg Asp
                610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
                660                 665                 670

Ala Lys His Glu Ala Gln Arg Leu Glu Gln Glu Ala Arg Gly Arg Leu
                675                 680                 685

Glu Arg Gln Lys Ile Leu Asp Gln Ser Glu Ala Glu Lys Ala Arg Lys
                690                 695                 700

Glu Leu Leu Glu Leu Glu Ala Leu Ser Met Ala Val Glu Ser Thr Gly
705                 710                 715                 720

Thr Ala Lys Ala Glu Ala Glu Ser Arg Ala Glu Ala Arg Ile Glu
                725                 730                 735

Gly Glu Gly Ser Val Leu Gln Ala Lys Leu Lys Ala Gln Ala Leu Ala
                740                 745                 750

Ile Glu Thr Glu Ala Glu Leu Gln Arg Val Gln Lys Val Arg Glu Leu
                755                 760                 765

Glu Leu Val Tyr Ala Arg Ala Gln Leu Glu Leu Glu Val Ser Lys Ala
                770                 775                 780

Gln Gln Leu Ala Glu Val Glu Val Lys Phe Lys Gln Met Thr Glu
785                 790                 795                 800

Ala Ile Gly Pro Ser Thr Ile Arg Asp Leu Ala Val Ala Gly Pro Glu
                805                 810                 815
```

```
Met Gln Val Lys Leu Leu Gln Ser Leu Gly Leu Lys Ser Thr Leu Ile
            820                 825                 830

Thr Asp Gly Ser Thr Pro Ile Asn Leu Phe Asn Thr Ala Phe Gly Leu
            835                 840                 845

Leu Gly Met Gly Pro Glu Gly Gln Pro Leu Gly Arg Arg Val Ala Ser
    850                 855                 860

Gly Pro Ser Pro Gly Glu Gly Ile Ser Pro Gln Ser Ala Gln Ala Pro
865                 870                 875                 880

Gln Ala Pro Gly Asp Asn His Val Val Pro Val Leu Arg
                885                 890
```

METHODS AND COMPOSITIONS FOR MAKING VAULT PARTICLES IN YEAST

CROSS-REFERENCE TO RELATED APPLICATIONS

This application claims the benefit of U.S. Patent Application No. 62/673,240, filed May 18, 2018, which is herein incorporated by reference in its entirety.

ACKNOWLEDGEMENT OF GOVERNMENT SUPPORT

This invention was made with government support under Grant Number 1647632, awarded by the National Science Foundation. The Government has certain rights in the invention.

REFERENCE TO A SEQUENCE LISTING SUBMITTED VIA EFS-WEB

The content of the ASCII text file of the sequence listing named "20190510_034044_181WO1_seq_ST25" which is 20.5 kb in size was created on May 10, 2019, and electronically submitted via EFS-Web herewith the application is incorporated herein by reference in its entirety.

BACKGROUND OF THE INVENTION

1. Field of the Invention

The present invention generally relates to methods and compositions for making vault particles.

2. Description of the Related Art

Known as the largest cytoplasmic ribonucleoprotein particles, vaults have been isolated from numerous eukaryotic species, whose structure is highly conserved and has a unique barrel-like morphology. The major vault protein (MVP) is the most abundant component of native vaults, and accounts for about 75% of the total protein mass in the particle. Seventy-eight copies of MVP are assembled into the barrel-like shell of the particle co-translationally on the polyribosome. Multiple copies of two additional protein components, vault poly(ADP-ribose) polymerase (VPARP) and telomerase-associated protein-1 (TEP1), and one or more copies of the non-coding vault RNA are found in native vault particles. Cryo-EM reconstruction of rat liver vaults treated with ribonuclease and vaults purified from VPARP and TEP1 knockout mice localized these three components to the inside of the vault lumen. Although the biological function of native vault particles and their components is still mysterious, vaults have been implicated in a broad range of cellular functions including innate immunity, multi-drug resistance, cell signaling, nuclear-cytoplasmic transport, mRNA localization, and nuclear pore assembly.

Expression of the cDNA encoding the MVP protein in insect cells using the baculovirus system is capable of directing the assembly of vault-like particles on polyribosomes. The empty recombinant vault particles have dimensions of 41×41×72.5 nm, and are virtually indistinguishable from native vaults when viewed under transmission electron microscopy (TEM). Differential cryo-EM mapping of engineered recombinant vaults with N-terminal or C-terminal tags showed that the C-termini of MVP were present at two ends of the particle facing outward, while the N-termini were buried at the particle waist.

Recombinant vaults are non-toxic, non-immunogenic, and biodegradable, which makes the particle an ideal carrier for macromolecules. Taking advantage of these properties, recombinant vaults have been engineered to enhance their functionality with various added domains to impart new activities like: cell targeting, cytoplasmic targeting, fluorescence, and amphiphilicity, which are being explored in therapeutic applications.

A strategy for packaging exogenous proteins into recombinant vault particles was developed by fusing these proteins to an MVP interaction domain termed INT or mINT. These two abbreviations, INT and mINT, are used interchangeably to refer to a 162-amino acid region found at the C-terminus of VPARP. This domain has a strong affinity for interaction with a segment of MVP that is localized in the vault interior, and acts as a packaging signal directing fusion protein into the vault lumen. Recombinant vaults, packaged with various components or containing various modifications at the cap and/or waist, are being analyzed for use in the medical field to reduce the growth of lung tumors and prevent *Chlamydia trachomatis* infections and for cell targeting and drug delivery in vitro.

Encapsulation of enzymes in recombinant vault particles can also improve their longevity and catalytic activities. Manganese peroxidase (MnP), which is a widely used lignin-degrading fungal enzyme in treating contaminants: like phenolics, aromatic hydrocarbons, and azo dyes, was packaged into vaults using the INT strategy. The packaged MnP showed better thermal stability than free MnPs and biotransformed phenol at a higher rate, suggesting vault encapsulation can serve as an approach for stabilizing biodegradative enzymes and delivering enzymatic bioremediation.

Current production of recombinant vault nanoparticles is only conducted in *Spodoptera frugiperda* (Sf9) insect cells as they are one of the few eukaryotes lacking endogenous vaults. Although production using insect cells can be scaled for commercial uses in the therapeutic arena, this approach is costly as it has been designed for human administration. Environmental use of engineered vaults will require a more facile production platform that will be significantly less costly than insect cell production and is easily integrated into existing industrial scale systems.

SUMMARY OF THE INVENTION

In some embodiments, the present invention is a host cell belonging to the Fungi Kingdom that has been recombinantly modified to contain a nucleic acid sequence that encodes a major vault protein (MVP). The major vault protein can be of any species, e.g., rat, mouse, monkey, human, etc. In some embodiments, the major vault protein is a human major vault protein. The host cell may contain one or more copies of the nucleic acid sequence. The one or more copies of the nucleic acid sequence may be codon optimized for expression in the given host cell. In some embodiments, the nucleic acid sequence comprises 85%, 86%, 87%, 88%, 89%, 90%, 91%, 92%, 93%, 94%, 95%, 96%, 97%, 98%, 99%, or 100% sequence identity to SEQ ID NO: 1. In some embodiments, the nucleic acid sequence is under the control of a promoter such as a constitutive promoter (e.g., PGAP or PAOXI), an inducible promoter, or a yeast promoter. In some embodiments, the host cell has been recombinantly modified to express one or more passenger peptides. In some embodiments, the host cell has been recombinantly modified to express one or more passenger peptides covalently linked to an mINT sequence. In some embodiments, the host cell is a yeast host cell. In some embodiments, the yeast host cell is a microorganism belonging to the family Saccharomycetaceae.

In some embodiments, the present invention is a method of making a major vault protein (MVP) in a host cell as described herein, which comprises culturing the host cell under conditions suitable for expression of the major vault protein. In some embodiments, the present invention is directed to a method of making a vault particle in a host cell as described herein, which comprises culturing the host cell under conditions suitable for formation of the vault particle. In some embodiments, the present invention is directed to a method of producing a commercial-scale amount of vault particles, which comprises culturing a host cell as described herein in a cell culture medium to obtain a host cell culture that is at or near a stationary growth phase. In some embodiments, the methods further comprise extracting the MVP and/or the vault particle(s) from the host cell(s). In some embodiments, the methods further comprise packaging one or more passenger molecules on or in the vault particle by (a) covalently linking the one or more passenger molecules to the N-terminus and/or C-terminus of the major vault protein, (b) mINT fusion packaging, and/or (c) passive packaging. In some embodiments, the methods comprise packaging one or more mINT passenger molecules within the cavity of the vault particle(s).

In some embodiments, the present invention is directed to a composition that comprises, consists essentially of, or consists of one or more host cells as described herein, one or more major vault proteins produced by a host cell as described herein, and/or one or more vault particles formed by a host cell as described herein.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DESCRIPTION OF THE DRAWINGS

This invention is further understood by reference to the drawings wherein.

DETAILED DESCRIPTION OF THE INVENTION

Figure 1:
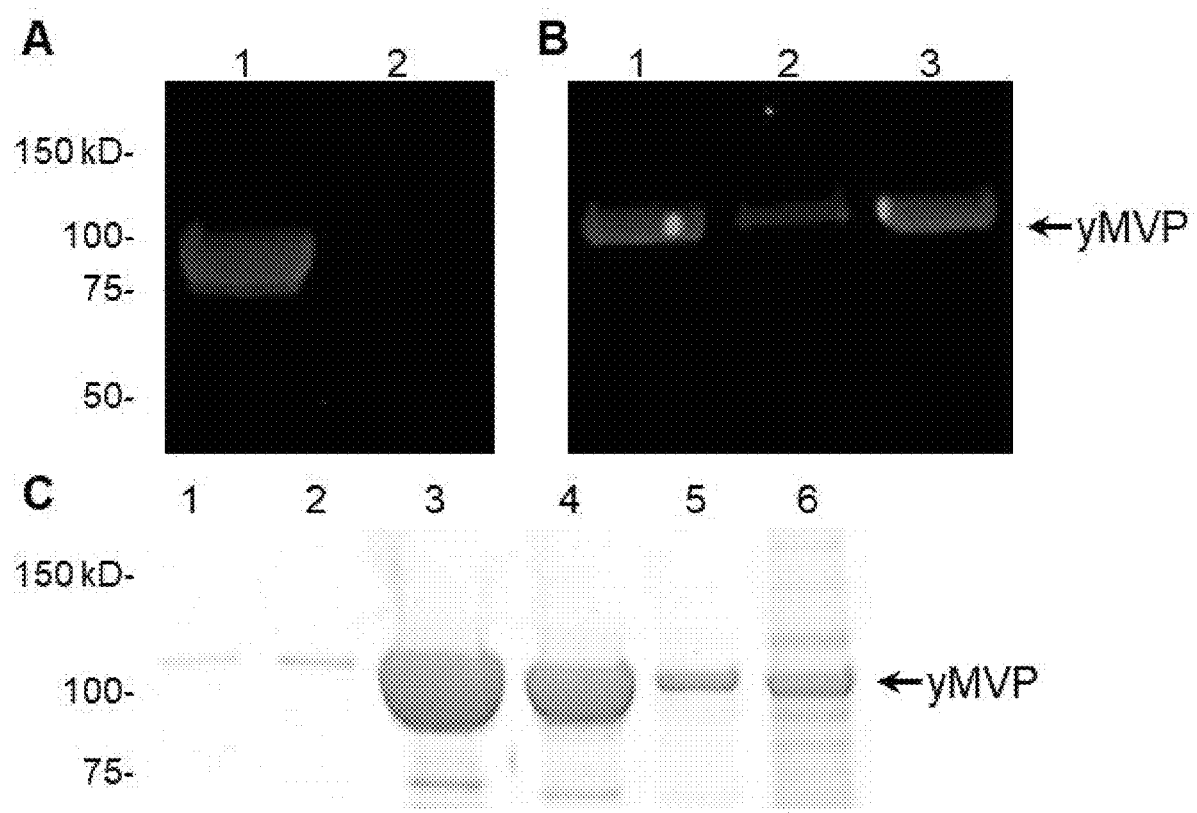
FIG. 1: Expression of yMVP in *P. pastoris* Culture. Panel A) S20 of transformed (lane 1) and native (lane 2) *P. pastoris* cell lysate were resolved on a 4-15% SDS-PAGE and visualized by Western blotting with anti-MVP antibodies. No band is observed in the lysate from native *P. pastoris* cells, while the lysate from yMVP-pGAPZA transformed *P. pastoris* shows a band at expected size (100 kD). Panel B) Western blot analysis of yMVP in different fractions separated by centrifugation. Lane 1: S20. Lane 2: S100. Lane 3: P100. Panel C) Distribution of yMVP in sucrose gradient. Lanes 1-6 correspond to sucrose fractions 20, 30, 40, 45, 50, and 60%. Equal volume of resuspended pellets from each sucrose fraction was loaded on the gel.

Yeast have been successfully used for several decades for the production of heterologous proteins of various origins including human for therapeutic proteins or derived from pathogens for use as vaccines. The production of heterologous proteins in yeast has advantages such as ease of microbial growth and cultivation on inexpensive growth media as compared to insect cells (summarized in Table 1).

TABLE 1

Comparison of Yeast and Insect Expression Systems

|  | Yeast | Insect |
|---|---|---|
| Cell growth | Rapid, $T_d{}^1$ about 2 hours | Slow, $T_d$ about 24 hours |
| Complexity of growth medium | Minimum | Complex |
| Cost of growth medium | Low, about $3.7/L | High, about $70/L |
| Protein folding | Refolding may be required | Proper folding |
| Vault production | Confirmed in this report | Proper assembly |

$^1T_d$: doubling time

Prior to the instant invention, expression of vault particles in yeast and/or production of commercial-scale quantities of vault particles in yeast has not been attained. The inability to obtain suitable expression of vault particles in yeast was believed to be due to the plurality of MVP proteins that are folded together to form the complex three-dimensional vault structure by polyribosomes. Specifically, once the mechanism of formation and assembly of vault particles was demonstrated to be carried out on polyribosomes in higher eukaryotic cells (Mrazek, et al. (2014) ACS Nano 8: 11552-11559), it was believed that the differences between the yeast ribosome and polysome and that of higher eukaryotes (Spahn, et al. (2001) Cell 107:373-386; and Mikamo, et al. (2005) J Struct Biol 151(1): 106-10) were significant such that expression and formation of vault particles in yeast was not previously obtained.

Nevertheless, as disclosed herein, after codon-optimization for expression in yeast and/or providing multiple copies of MVP cDNA to yeast, commercial-scale expression of vault particles can be obtained using yeast. As used herein, "commercial-scale" and "large-scale" are used interchangeably to refer to at least 5 mg of vault particles produced per liter of a host cell culture at or near its stationary growth phase, preferably at its stationary growth phase. As used herein, "host cell culture" refers to cell culture media comprising host cells that have been recombinantly modified to comprise one or more exogenous MVP sequences and cultured to express the one or more exogenous MVP sequences. In some embodiments, the commercial-scale amount of vault particles is at least about 6 mg/L of a host cell culture at or near its stationary growth phase, preferably at its stationary growth phase. A host cell culture is "near" its stationary growth phase after its exponential growth phase and before its stationary growth phase. In some embodiments, the commercial-scale amount of vault particles is at least about 7 mg/L of a host cell culture at or near its stationary growth phase, preferably at its stationary growth phase. In some embodiments, the commercial-scale amount of vault particles is at least about 8 mg/L of a host cell culture at or near its stationary growth phase, preferably at its stationary growth phase. In some embodiments, the commercial-scale amount of vault particles is at least about 9 mg/L of a host cell culture at or near its stationary growth phase, preferably at its stationary growth phase.

Commercial-Scale Up of Vault Particle Production

As described herein, commercial-scale quantities of vault particles were produced and assembled in the eukaryotic yeast *Pichia pastoris*. These "yeast vaults" share similar morphology and properties with vault particles produced in Sf9 insect cells. mINT passenger molecules were successfully packaged within the cavities of the yeast vaults and the packaged passenger molecules exhibited their given functional activity (i.e., the functional activity of the "free" passenger molecule without being covalently linked to the mINT sequence").

*P. pastoris* retains all the advantages of expression in *S. cerevisiae*, but can yield higher levels of expressed protein. This methylotrophic yeast can drive expression from a constitutive promoter, e.g., the promoter of the glyceraldehyde-3-phosphate dehydrogenase gene ($P_{GAP}$) or the promoter of the alcohol oxidase I gene ($P_{AOX1}$), which is one of the strongest regulatory promoters known. These expression cassettes are integrated at specific sites in the *P. pastoris* genome, either singly or in multiple copies. Furthermore, *P. pastoris* is easy to grow to very high densities in fermenters, ensuring high levels of recombinant protein production.

Although production of yeast vaults is exemplified herein using *P. pastoris*, the use of other yeast hosts is contemplated herein. For example, as contemplated herein, any member of the family Saccharomycetaceae can be used to produce yeast vaults according to the present invention.

yMVP Expression Vector

For expression in *Pichia pastoris* (*P. pastoris*), rat and human MVP coding sequences were codon optimized and cloned under the control of the glycerol aldehyde promoter ($P_{GAP}$), which is a strong constitutive promoter in the pGAPZ vector (Invitrogen) that also expresses ZEOCIN for antibiotic selection. Recombinant pGAPZ-rMVP and pGAPZ-hMVP plasmids were transformed into *E. coli* HST08 cells (TaKaRa) and selected for ZEOCIN resistance. Colonies resistant to ZEOCIN (25 µg/mL) were grown overnight, and plasmid DNAs were sequenced to confirm the MVP cDNA sequences were not altered. Afterwards, plasmid DNAs from positive clones of pGAPZ-MVP (one for rMVP and another for hMVP) were purified from large-scale cultures and linearized with BspHI for yeast transformation.

Although use of the pGAPZ vector is exemplified herein, other expression vectors and selectable markers (such as G418, hygromycin, nourseothricin, blasticidin, auxotrophic markers like HIS4, ARG4, ADE1, or URA3, etc.) in the art may be used. Alternatively, inducible promoters such as $P_{AOX1}$ and $P_{FLD}$ (which are induced by methanol and methylamine, respectively), or constitutive promoters such as UPP and TEF1 may be used. In fact, the inducible promoter, $P_{AOX1}$ was used to successfully drive expression of vault particles in *Pichia* spp.

Any organism belonging to the Saccharomycetes class of the fungus kingdom may be used as a host cell to produce vault particles and, based on the organism selected as the host cell and the conditions under which expression is to be effected, those skilled in the art can readily select a suitable promoter to drive the expression of the given MVP sequence. For example, the pKLAC1 expression vector (New England Biolabs) may be used to place expression of the given MVP sequence under the control of the constitutive LAC4 promoter to produce vault particles in *K. lactis*.

Additionally, any method in the art (e.g., electroporation, microinjection, gene gun, infectious agent mediated delivery, CRISPR, etc.) may be used to insert one or more copies of a given MVP sequence into a given host cell. The one or more copies of the given MVP sequence may be integrated into the host cell's genome. As an example, any yeast integrating plasmid (YIp) in the art may be used to integrate one or more copies of a given MVP sequence directly into the chromosome of a yeast host cell via homologous recombination. Alternatively, the one or more copies of the given MVP sequence may be inserted into the host cell without becoming integrated into the host cell's genome, e.g., remain as separate nucleic acid molecules in the cytoplasm. As an example, any yeast replicating plasmid (YRp), any yeast centromere plasmid (YCp), and any yeast episomal plasmid (YEp) in the art may be used to insert one or more copies of a given MVP sequence into a yeast host cell without incorporating the given MVP sequence into the yeast host cell's chromosome.

Stably Transformed Yeast Hosts that Express MVPs and Assemble Vault Particles

The *Pichia pastoris* protease-deficient strain SMD 1168 was transformed by electroporation with linearized pGAPZ-MVP plasmids (one for rMVP and another for hMVP). In general, yeast competent cells are first transformed with a given MVP sequence (e.g., by electroporation, heat shock, gene gun etc.) and then allowed to recover in a nutrient or high sugar medium and then the cells are plated on a selection media containing the given antibiotic used for selection of the transformed host cells. For SMD 1168, transformants were selected using YPDS agar containing three different concentrations of ZEOCIN (100, 500, and 1,000 µg/ml). Colonies were allowed to grow up at 30° C. for 5-7 days. Ten transformants (5 for pGAPZ-rMVP and 5 for pGAPZ-hMVP) were selected for further analysis. Colonies were resuspended in YPD media comprising 100 µg/ml ZEOCIN and fermented for about 96 hours at cells with shaking at 200 rpm. Aliquots were collected from shake cultures at 0, 24, 48, 72, and 96 hours, and the cells were pelleted. Extracts from cell pellets were for analyzed for MVP expression. Western blot analysis revealed that four of the five colonies expressed hMVP.

The clone that expressed the highest level of hMVP was further characterized and it was found that intact vault particles were being formed. However, the level of expression and the yield was very low compared with expression of hMVP in insect cells. One explanation for the low level of expression could be due to codon bias between human and yeast cells. Therefore, the human MVP protein sequence was codon optimized for expression in *Pichia pastoris* (see, e.g., U.S. Pat. No. 8,326,547, which is herein incorporated by reference in its entirety) and the codon optimized cDNA was cloned into GenScript's *Pichia* expression vector pPICZ A under control of the $P_{AOX1}$ promoter which is methanol inducible. The yMVP cDNA was subcloned into the pGAPZ vector so that the codon optimized yMVP cDNA was under the control of the $P_{GAP}$ promoter. Although use of the $P_{GAP}$ promoter is exemplified herein, other promoters known in the art may be selected based on the given yeast host and expression vector and desired level and control of expression.

Figure 7:
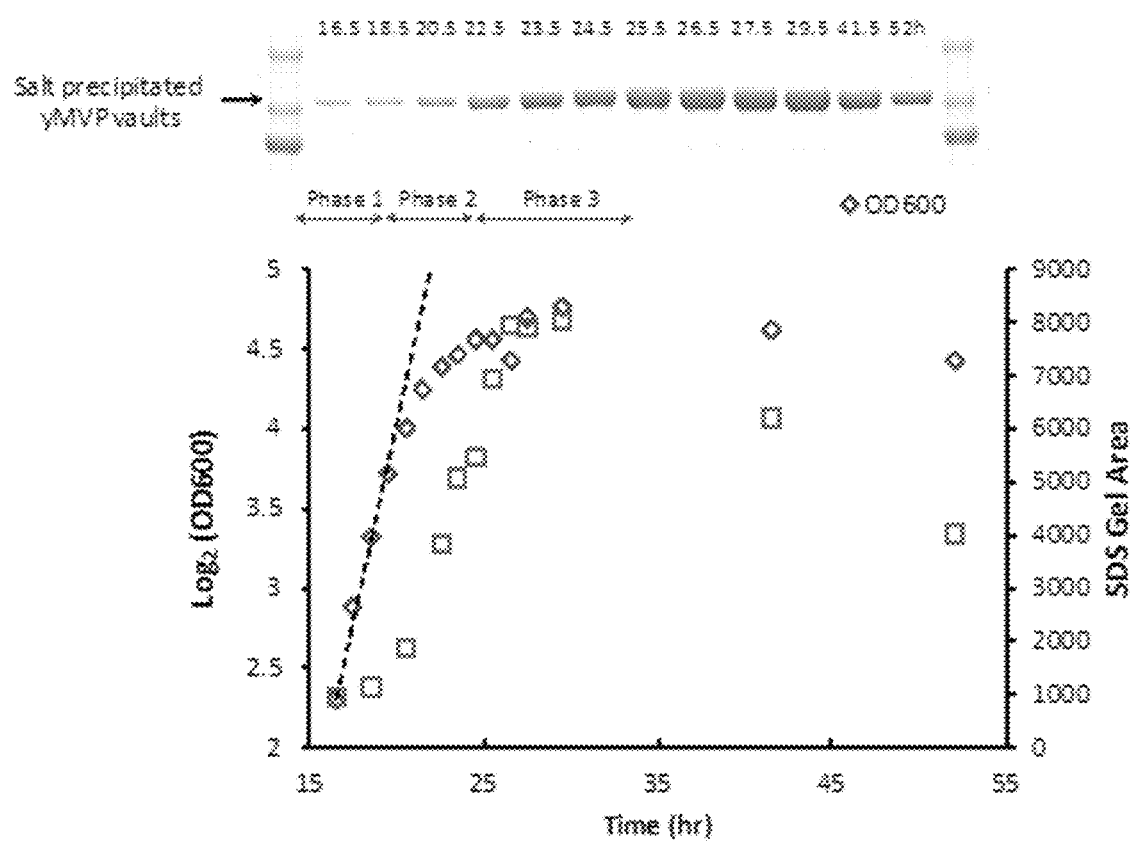
FIG. 7: Growth phase analysis comparing density over time with MVP protein expression in yeast. Diamonds are OD600 and squares are relative density units.

The *P. pastoris* protease-deficient strain SMD 1168 was transformed with linearized pGAPZ-yMVP plasmid DNA containing a codon optimized human MVP (OP-hMVP) cDNA and ZEOCIN resistant colonies were selected and analyzed for MVP expression. Total cell extracts were prepared and analyzed by Western blot. One candidate was further characterized and determined to be producing fully assembled vault particles. A time course of expression was carried out (FIG. 7).

Vault particles composed of either rMVP or hMVP were successfully produced in a non-protease-deficient strain, i.e., BG10. The *Pichia pastoris* wild-type BG10 (BioGrammatics) strain was transformed by electroporation with linearized pJUG plasmid (BioGrammatics) DNA containing a codon optimized human MVP (OP-hMVP) cDNA. The pJUG plasmid contains the constitutive UPP promoter to drive expression of the MVP sequence and a G418 resistance gene for selection. Four transformants were selected for analysis. Transformants were inoculated into 2 ml of YPD media, grown at 30° C. for 24 hours. Cells were pelleted and extracts were analyzed for MVP expression by Western blot. All of the transformants expressed MVP.

The BG10 strain was also transformed by electroporation with linearized pPICZ-codon optimized human MVP (OP-hMVP) plasmid. The pPICz plasmid contains the methanol inducible AOX promoter to drive expression and the gene for ZEOCIN selection. Twenty transformants were selected from culture plates comprising 1 mg/ml ZEOCIN and used for further analysis. Transformants were inoculated into 2 ml of BMGY media, grown at 30° C. for 24 hours. Cells were collected and resuspended in BMMY (media contains 1% methanol), grown at 30° C., after 24 hours, 1% methanol was added to the culture and incubation continued for an additional 24 hours. Cells were pelleted and extracts were analyzed for MVP expression by Western blot and quantitative ELISA. All of the transformants expressed hMVP.

The BG10 strain was also transformed by electroporation with linearized pGAPZ-OP-hMVP plasmid. The pGAPz plasmid contains the constitutive GAP promoter. Twenty transformants were selected for analysis from culture plates comprising 1 mg/ml ZEOCIN. Transformants were inoculated into 2 ml of YPD media, grown at 30° C. for 24 hours, and the cells were pelleted. Extracts from cell pellets were analyzed for MVP expression by Western blot and quantitative ELISAs. Expression analysis revealed that 16 of the 20 colonies expressed hMVP.

Figure 8:
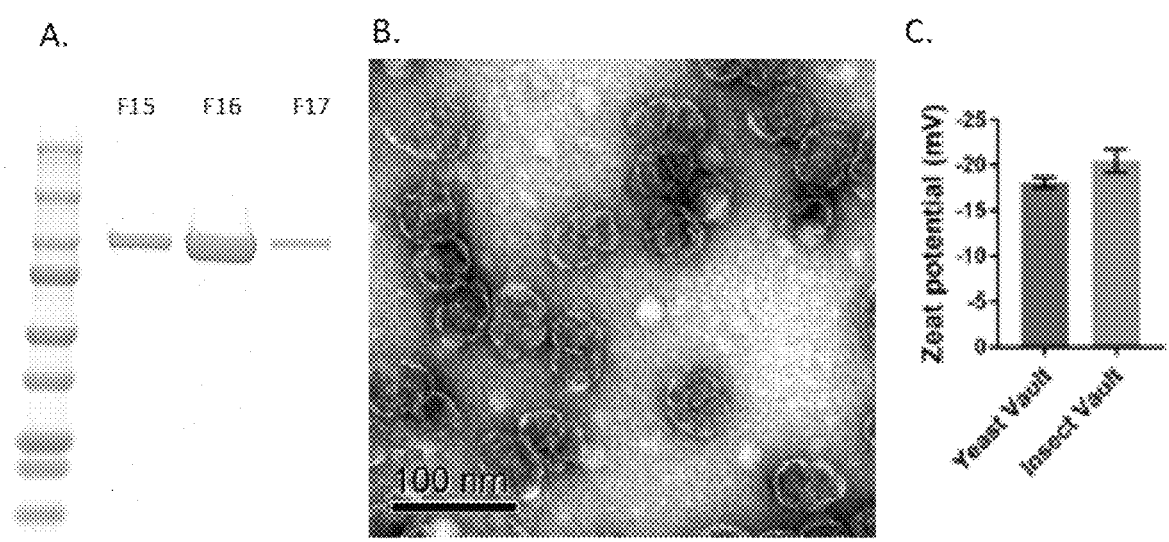
FIG. 8: FPLC purification of vault particles produced in yeast. Panel A) Coomassie stained SDS-PAGE of peak FPLC fractions. Panel B) Electron micrograph of negatively stained vault particles. Panel C) Zeta potential measurement of vaults produced in yeast and insect cells.

Yeast vaults were purified by fast protein liquid chromatography (FPLC) on a TMAE Fractogel column. Purified vaults were applied to carbon grids, stained with uranyl acetate, and visualized using standard transmission electron microscopy (FIG. 8). Yeast produced vaults showed indistinguishable morphology, structure, and size compared to insect cell-produced vaults. They also had similar zeta potentials which measures the overall charge of particles. Ideally, a yield of about 5 mg of assembled vaults per liter of yeast cell culture was desired as a positive result. Unexpectedly, the actual yields were about 7-9 mg/L of yeast cells culture. That is, the actual yields were about 40% to about 80% greater than that expected.

Therefore, these experiments show that vault particles can be readily produced in yeast cultures faster and at similar or better concentration levels than they can be produced in insect cell cultures. See Table 2.

TABLE 2

Summary of yeast versus Sf9 cell production

| | Yeast Host Cells | Sf9 Host Cells |
|---|---|---|
| Vault Production | Yes | Yes |
| Yield | ~8 mg/L | ~10 mg/L |
| Time | 1-1.5 Days | 3-4 Days |
| mINT Fusion Packaging | Yes | Yes |
| Average Number of mINT Passenger Molecules per Vault Particle | 45.7 | Similar number |

Although the production of vault particles comprising rMVP (or MVP proteins of other species) in yeast was not pursued, it is believed that codon optimization of the rMVP cDNA (or MVP sequences of other species) will similarly result in the production of vault particles in a yeast host.

Packaging of MnP-INT into Yeast Vaults and Functional Analysis

The INT domain, which is located at the C-terminus of VPARP, is responsible for binding to the interior of the MVP shell. By attaching it to heterologous components, the INT domain serves as a packaging signal and the fused proteins into the vault particle. As a first step to demonstrate the feasibility of packaging vault cargo, a monomeric protein with red fluorescent properties, mCherry was selected. mCherry is used as a marker when tagged to molecules or cellular components. The protein is about 29 kDa with peak fluorescent excitation and emission at 587 nm and 610 nm, respectively. It matures quickly allowing it to be visualize soon after translation. mCherry demonstrates the packaging efficacy of vault particles.

Figure 9:
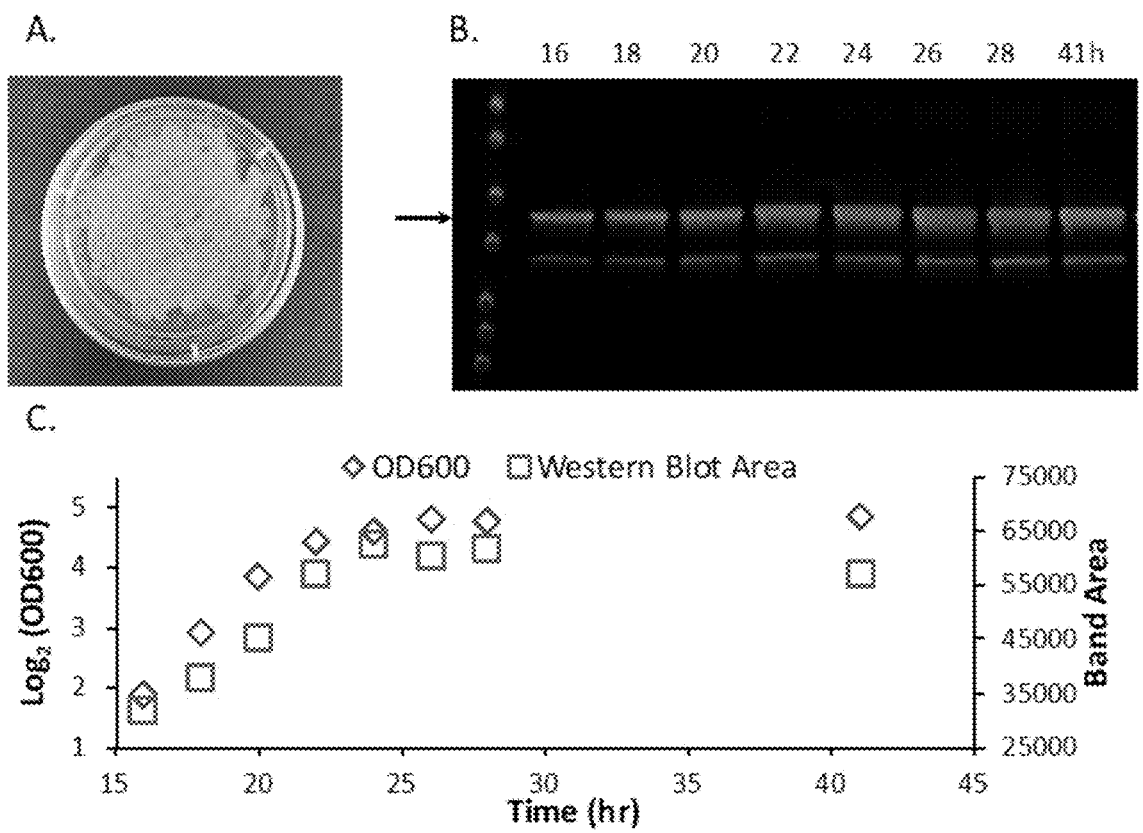
FIG. 9: Yeast expression of mCherry-INT. Panel A) Plate of yeast expressing mCherry-INT. B) Western blot analysis of mCherry-INT expression at the indicated times. C) Yeast density growth measurement.

A codon optimized mCherry-INT was synthesized by GenScript and subcloned into pGAPZ. mCherry was chosen as its pink color is also visible to the naked eye. P. pastoris protease deficient strain, SMD1168 was transformed with linearized pGAPZ-mCherry-INT plasmid DNA and ZEO-CIN resistant colonies were selected and analyzed for expression. Because the colonies turn pink from expressing mCherry-INT, one is able to visually select colonies. A time course of expression was carried out (FIG. 9). Total cell extracts were prepared and analyzed by Western blot using our anti-INT polyclonal antibody to confirm expression of the mCherry-INT fusion protein.

Figure 10:
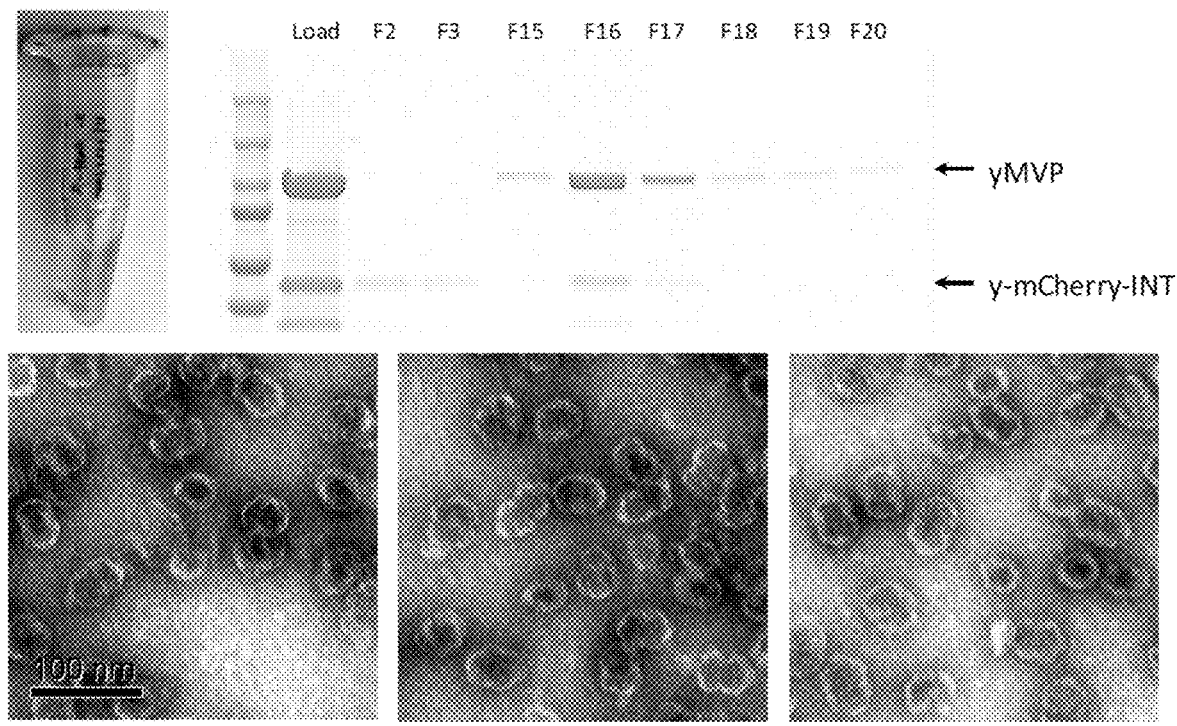
FIG. 10: FPLC purification of y-mCherry-INT/yMVP vaults. Upper left, purified "pink" vault particles. Upper right, Coomassie stained SDS-PAGE of FPLC fractionations. Bottom, Electron micrographs of negatively stained purified "pink" vault particles.

The mCherry-INT expressed in yeast was packaged into yeast vaults and the particles were purified by the FPLC procedure in the art. The purified vaults were analyzed on SDS-PAGE, electron microscopy and the number of copies of mCherry-INT packaged per vault particle was determined by a quantitative ELISA assay. As there are 78 copies of MVP per vault particle and there is a single binding site for INT per MVP the maximum number of copies of mCherry-INT a vault particle can comprise is 78. It was determined that there were 46 copies of mCherry-INT per vault particle, which is comparable to that observed for vault particles produced in insect cells. The purification results are shown in FIG. 10.

The non-specific enzyme, manganese peroxidase (MnP), which has been isolated from many wood colonizing and soil colonizing fungi, is an attractive candidate for enzymatic degradation, due to its high oxidative ability. MnP was used as the proof-of-concept enzyme in this project to assess the performance of yeast vaults as a packaging vehicle. Nevertheless, any desired passenger molecule may be packaged in yeast vaults by, for example, mINT fusion packaging or passive packaging. Nevertheless, in some embodiments, mINT fusion packaging is preferred.

Figure 11:
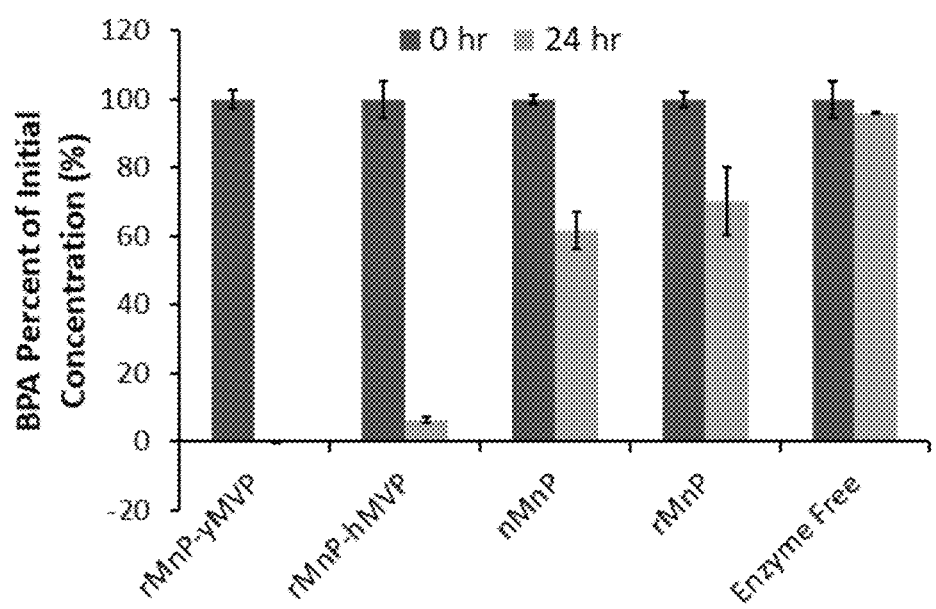
FIG. 11: Biodegradation of BPA by vault-packaged MnPs and unpackaged MnPs in 24 hours. All enzymes were dosed at 29 U/L initial activity. BPA degradation was higher in reactions catalyzed by MnP packaged in yMVP vaults or insect-produced hMVP vaults. The bars in each set from left to right are 0 hours and 24 hours.

Recombinant MnP-INT (rMnP) was produced in insect Sf9 cells and packaged into yeast vaults following standard vault packaging and purification protocols. Biodegradation of bisphenol-A (BPA), as a model water contaminant reported to cause endocrine disruption and reproductive toxicity, was tested to confirm the activity and catalytic performance of yeast vaults packaged rMnP (rMnP-yMVP). As shown in FIG. 11, after 24-hour reactions, over 95% of BPA was degraded after rMnP-yMVP treatment, and the residual BPA concentration was below the detection limit. Treatment by rMnP packaged in insect produced vaults (rMnP-hMVP) also resulted in 94% BPA degradation. In contrast to the high BPA degradation rate observed for vault-packaged rMnPs, unpackaged MnPs, including rMnP and native MnP (nMnP) purified from fungal cultures, only resulted in 30% and 38% BPA removals, respectively. These results suggest MnP packaged in yeast vaults maintains it enzymatic activity and exhibits significantly better biodegradation of BPA than unpackaged MnP, indicating yeast vaults have similar functionality and properties as insect produced vaults in packaging enzymes and improving their performance. Similarly, the fungal enzyme laccase maintained its enzymatic activity when packaged in yeast vaults.

Based on these experiments, there were no functional differences between vault particles produced in yeast as compared to vault particles produced in insect cells. Nevertheless, because yeast vaults are not made using insect cells, yeast vaults do not contain contaminants, e.g., undesired proteins, cellular debris, and other biomolecules, that originate from insects. mCherry-INT was packaged at the same efficiency in yeast produced vaults as in insect produced vaults. MnP-INT packaged in vault particles produced in yeast also maintained activity, and showed significant better bisphenol A biodegradation than unpackaged MnP.

In some embodiments, the methods comprise recovering or purifying an mINT passenger molecule from a yeast host cell. In some embodiments, the mINT passenger molecule is secreted into the cytoplasm of the yeast host cell and the mINT passenger molecule is recovered or purified therefrom. In some embodiments, the mINT passenger molecule is secreted by the yeast host cell and the mINT passenger molecule is recovered or purified from the culture medium.

Expression of yMVP

Although vault particles have been isolated from numerous eukaryotic organisms, yeast, worms, insects, and plants all lack endogenous vaults. In fact, no MVP homologue has been detected in the genome of these organisms. Thus, as expected, the native yeast P. pastoris cells did not contain MVP protein (FIG. 1, Panel A, lane 2). The human MVP coding sequence was expressed under the control of the constitutive promoter, $P_{GAP}$. Unlike the other commonly used $P_{AOX1}$ promoter, which is only induced by methanol and strongly repressed by other carbon sources, such as glucose, ethanol and glycerol, $P_{GAP}$ is constitutively active such that the gene under its control is continuously expressed, although the expression is affected by the carbon source used for culture. Glucose, the main carbon source used in YPD medium, was proven to provide good expression under the $P_{GAP}$ promoter.

P. pastoris (yMVP-pGAPZA) cells were grown in YPD medium for 30 hours at this point the culture reached stationary phase. Cells were then collected, lysed, and centrifuged and the supernatant, S20, was analyzed for expression. As shown in lane 1 in FIG. 1, Panel A, a significant amount of yMVP was detected in the S20 of cell lysate at the expected size (about 100 kD) while no yMVP was detected in non-transformed *P. pastoris*, showing that yMVP was expressed under the $P_{GAP}$ promoter in *P. pastoris* and stayed in the soluble fraction. Afterwards, the S20 was centrifuged at 100,000×g to pellet large complexes, followed by fractionation on a step sucrose gradient using methods in the art. Following fractionation at 100,000×g, a small amount of yMVP remained in the S100 (lane 2 in FIG. 1, Panel B), while the majority of yMVP was in the P100 (lane 3 in FIG. 1, Panel B), paralleling expression patterns seen in insects and native mammalian cells. The yMVP in P100 were assumed to be the assembled vault particles, while yMVP in the S100 probably resulted from incompletely assembled vaults or degradation products. Analysis of sucrose gradient fractions (FIG. 1, Panel C) showed that the distribution of yMVP was consistent with the pattern observed for recombinant vaults from insect cells and native vaults from various tissue culture cell lines. The yMVP was detected throughout all sucrose layers, but was found to be most abundant in the 40 and 45% fractions, where the assembled intact vault particles are usually found.

Formation of Vault Particles

Figure 2:
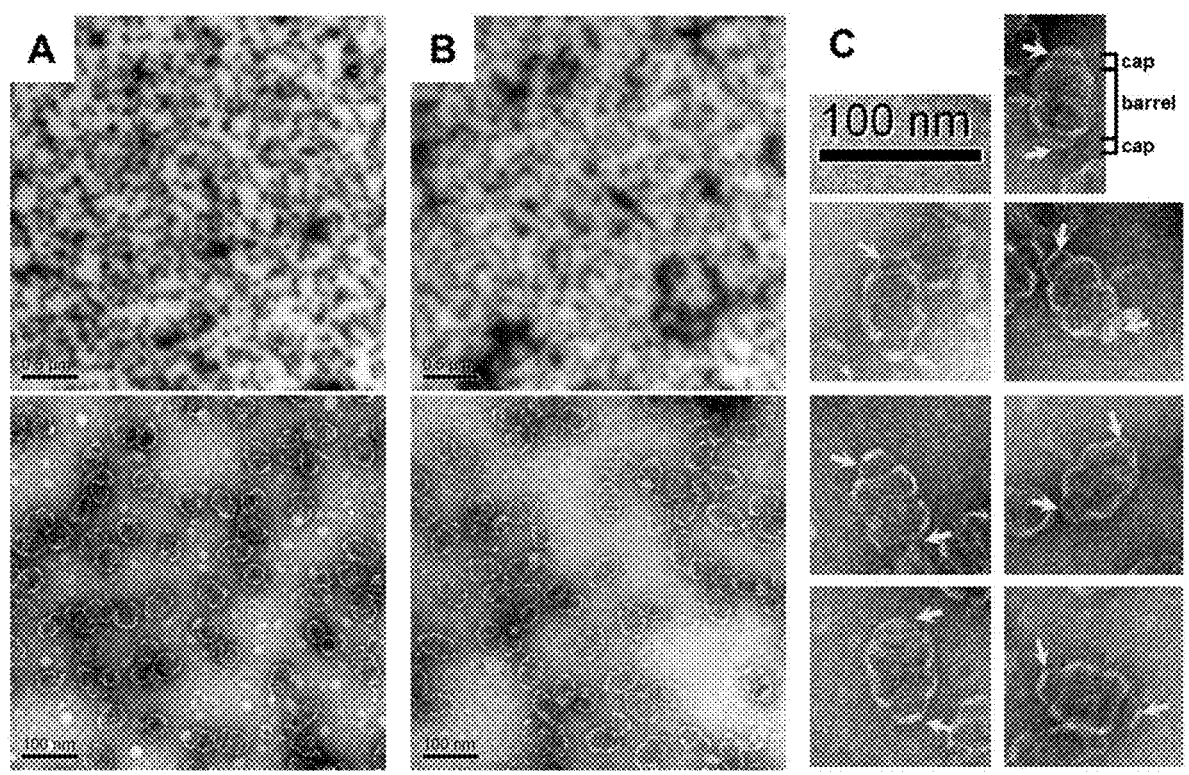
FIG. 2: Recombinant Vault Particles Assembled in Yeast *P. pastoris* Expressing yMVP. Panel A) Recombinant vault particles purified from *P. pastoris* culture (yeast vaults). Panel B) Recombinant vault particles purified from insect Sf9 cells (insect vaults). Panel C) Zoom-in view of individual yeast vaults. Yellow arrows (arrows at ends) indicate the caps, and blue arrows (middle arrows) indicate the waists of the yeast vaults.

The 40 and 45% sucrose fractions were examined by TEM and found to contain abundant vault particles and some contaminating ribosomes. The particles were further purified by anion-exchange chromatography prior to viewing by TEM. The morphology of the TEM images demonstrated that yeast cells were able to synthesize and assemble yMVP into intact vault particles. FIG. 2, Panel A shows the typical negatively stained yeast vaults observed at two magnifications. The isolated vaults were indistinguishable from vaults produced by insects (FIG. 2, Panel B) or endogenous vaults found in various organisms. Each particle had two caps and a barrel-like body (FIG. 2, Panel C). The waist area, where the two vault halves come together was narrower than the rest of the barrel body. These particles were about 64 nm (±3 nm, n=30) in length and 36 nm in width (±2.5 nm, n=30), which are smaller than the 75 nm×42 nm structure resolved by Cryo-EM and the 67 nm×40 nm structure resolved by X-ray diffraction. The decrease in vault size in TEM images was also observed for insect vaults, which is probably due to the shrinking of particles during air-drying or a compression resulting from deposited uranyl acetate. Although most yeast vaults were similar in size and had consistent length, variations in width were still observed. Some vault particles exhibited wider barrel-like structures than normal vaults, which were similar to protease treated vault particles purified from rat liver.

Production of yMVP and Assembled Vault Particles

The $P_{GAP}$ promoter allows for constitutive expression of yMVP in *P. pastoris* cells.

Figure 3:
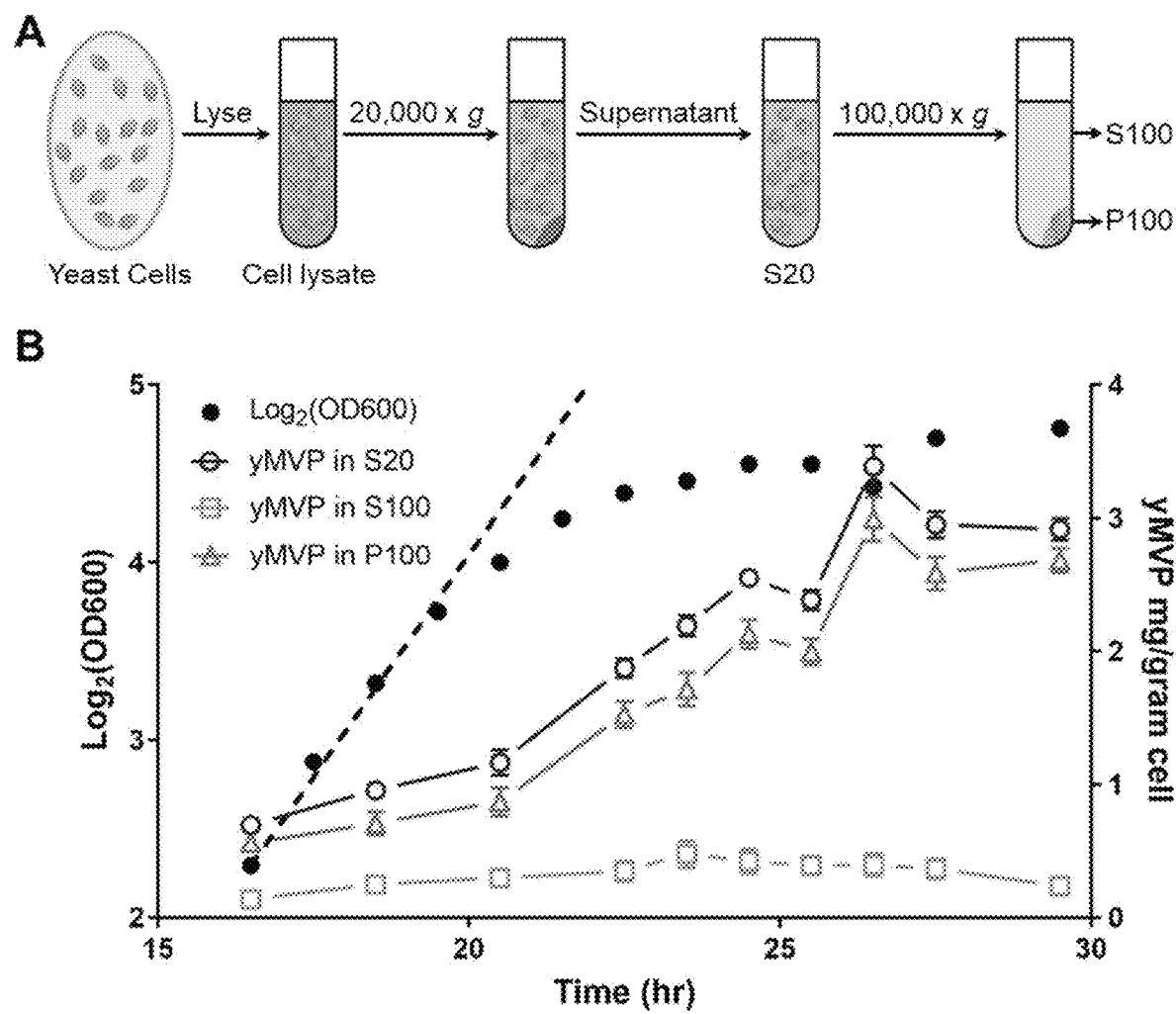
FIG. 3: Accumulation of Cell Biomass and yMVP in *P. pastoris* Culture. Panel A) Schematic of yMVP crude lysate preparations by centrifugation. Panel B) Yeast growth curve and expression of yMVP over time. Samples were collected hourly from 16.5 to 27.5 hours plus at 29.5 hours for recording OD. The dash line represents the OD trend assuming the culture keeps growing exponentially. Samples were collected at 16.5, 18.5, 20.5, 22.5, 23.5, 24.5, 25.5, 26.5, 27.5, and 29.5 hours for analyzing S20 and S100. The amount of yMVP in S20 and S100 fractions was determined using Q-ELISA, and normalized to cell biomass. Concentrations of yMVP in P100 were calculated by subtracting yMVP in S100 from S20. Error bars represent one standard deviation (n=6-12).
Figure 4:
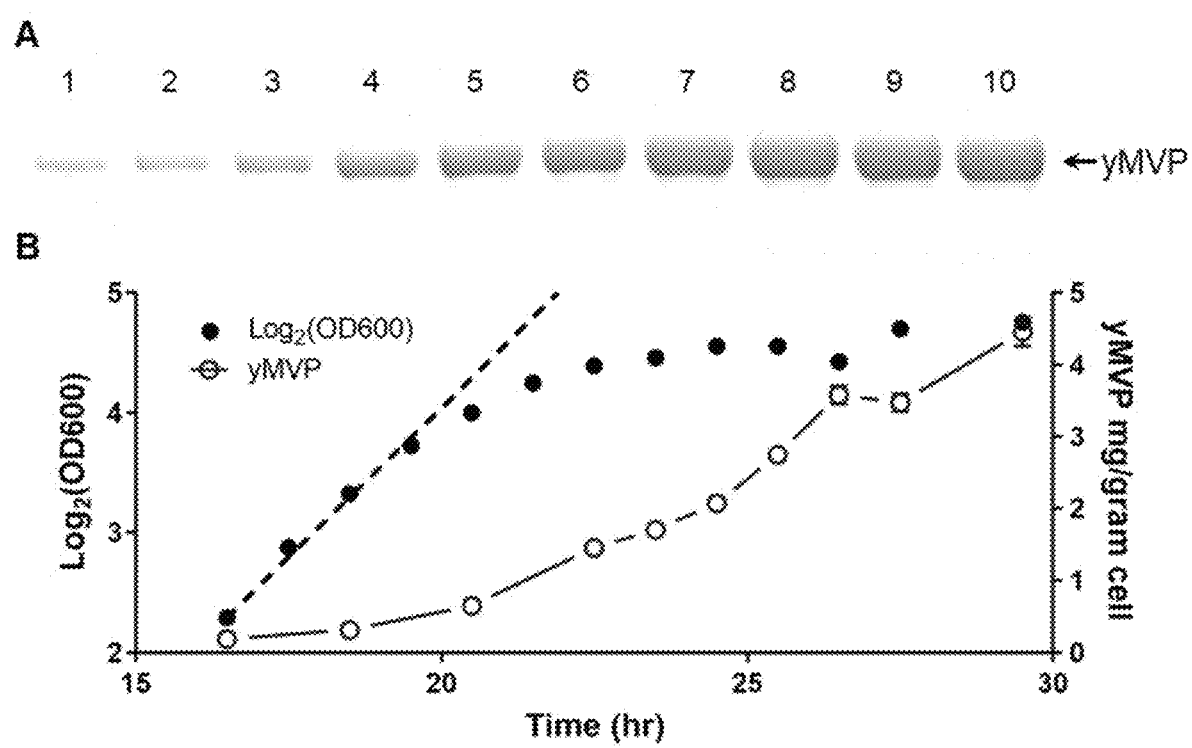
FIG. 4: Accumulation of Assembled Vault Particles in *P. pastoris* Culture. Panel A) Yeast vaults were partially purified by salt precipitation, and resolved on SDS-PAGE followed by Coomassie staining. Lane 1-10 correspond to samples collected at 16.5, 18.5, 20.5, 22.5, 23.5, 24.5, 25.5, 26.5, 27.5, and 29.5 hours. Panel B) Quantitative analysis of salt precipitated yMVP over time. The concentrations of yMVP were determined using Q-ELISA, and normalized to cell biomass. Error bars represent one standard deviation (n=6).

To access the accumulation of yMVP and assembled yeast vaults, yMVP in S20, S100, and P100 fractions was quantified at various time points ranging from 16.5 hours to 29.5 hours by ELISA. S20 was ultra-centrifuged and separated into two fractions: S100 and P100 (FIG. 3, Panel A). Yeast MVP in S100 is likely from degraded or incomplete vault particles, while yMVP in P100 is believed to be assembled vaults. Although yMVP in P100 was not directly analyzed using ELISA, it was calculated as the difference between S20 and S100. Optical density at 600 nm (OD600) was also recorded to determine cell growth phase. As shown in FIG. 3, Panel B, the *P. pastoris* (yMVP-pGAPZA) culture was in exponential phase between 16.5 hours and 19.5 hours, and started to transition to stationary phase at 19.5 hours. At about 23.5 hours, the culture reached stationary phase, and the OD maintained around 23. Concentrations of yMVP in S20 and P100 changed significantly overtime, but not following similar OD pattern. FIG. 3, Panel B shows that yMVP continuously accumulated in S20 and P100 from 16.5 hours to 26.5 hours, and reached 3.4 and 3.0 mg/g yeast cells, respectively, suggesting the yeast vaults were continuously accumulated in the cell until 26.5 hours. This was also supported by the increase of yMVP in salt precipitated fractions, which were partially purified assembled vault particles (FIG. 4).

The yield of assembled yeast vaults was low in exponentially growing cells but continued to increase until the cultures reached mid-stationary phase (OD about 20). This was somewhat surprising as vault synthesis and assembly were expected to cease after the exponential phase. Vault particles have been shown to be synthesized and assembled on polyribosome structures in insect cells. However, previous studies on yeast polyribosomes found that polyribosomes could only be isolated from cells in the log phase and the cultures grown into the stationary phase lacked polyribosomes. Although it is possible that vaults are assembled by a different mechanism in yeast, it is highly likely that the presence of numerous yMVP mRNAs alters the profile and life of polyribosomes in *P. pastoris* cells. Polyribosomes in eukaryotic cells form progressively on mRNAs, experiencing three main conformations including circle, line, and 3D helices. During the first few rounds of translation, ribosomes are gradually loaded on the mRNAs, inducing mRNA conformational change and forming the initial circular and linear polyribosomes. As translation rounds increase, more ribosomes are loaded on the mRNA, and the circular and linear polyribosomes are transformed into densely packed 3D helices. The formation of highly ordered vault structures requires co-translation of multiple MVP peptides on a single MVP mRNA one following another without break for dozens of rounds. Therefore, the polyribosome structure associated with vault MVP mRNA is likely to be the highly condensed 3D helices, rather than the linear or circular conformation. The compact 3D helical polyribosomes could shield mRNA inside from being cleaved by ribonucleases and thus extend the life of the MVP mRNA and the life of the polyribosomes as well (Brandt et al., 2010). Additionally, the polyribosomes aligned on MVP mRNA might organize in a certain way to optimize the folding of MVP and reduce nascent MVP aggregation and degradation, which might also contribute to their longevity in cells.

Comparison Between Yeast Vaults and Insect Vaults

So far, vaults have been heterologously expressed in two eukaryotic hosts that lack endogenous vaults: yeast and insect cells. The basic physical and chemical properties between vaults produced in these two systems was next compared to understand whether the expression host affects the structure and properties of vaults. As shown in FIG. 2, Panels A and B, the morphology and shape of vaults produced in both systems were very close to each other, with two caps and a barrel-like body in the middle. Both vault particles are negatively charged and had a similar zeta potential around −19 mV (data not shown).

Sequestering of INT-Fused Proteins into Yeast Vaults

The vault particle has been developed as a delivery system. The particle acts like a vehicle and is large enough to carry multiple copies of macromolecules or other complexes. To sequester exogenous components into the vault lumen, INT binding is the commonly used strategy. As a first step to demonstrate the feasibility of packaging vault cargo, a monomeric protein with red fluorescent properties, mCherry was selected. mCherry is used as a marker when tagged to molecules or cellular components. The protein is about 29 kDa with peak fluorescent excitation and emission at 587 nm and 610 nm, respectively. It matures quickly allowing it to be visualized soon after translation. mCherry has been used in previous insect cell line development to test vault packaging effectiveness.

Figure 5:
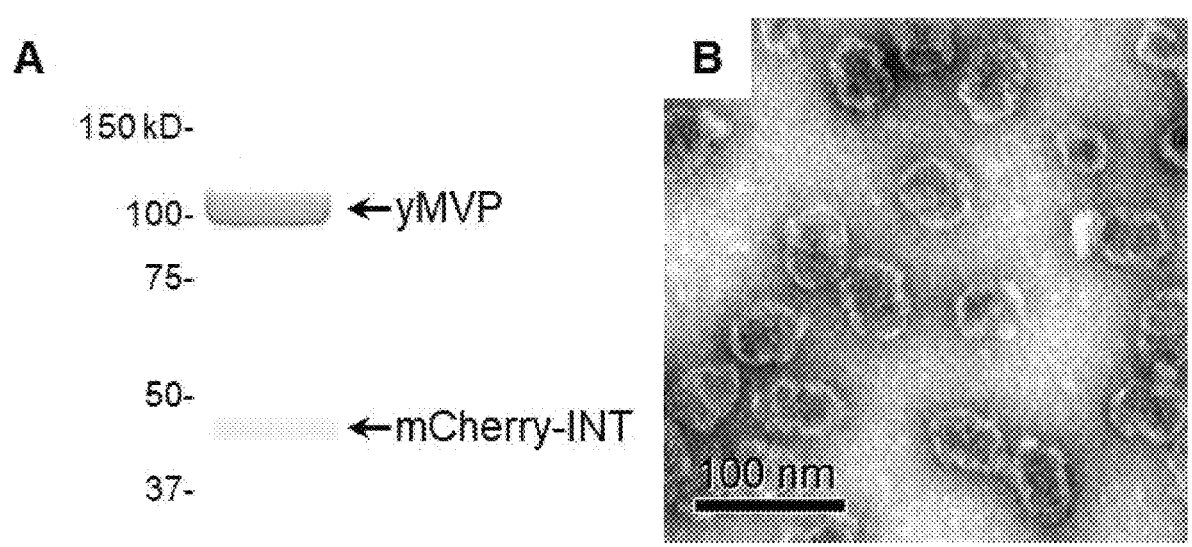
FIG. 5: Packaging of INT-fused proteins into yeast vaults. Purified yeast vaults packaged with mCherry-INT were fractioned on 4-15% SDS-PAGE and analyzed using Coomassie staining (Panel A) and viewed under TEM (Panel B).

As shown in FIG. 5, Panel A, significant amounts of mCherry-INT were co-purified with vaults produced in *P. pastoris*, suggesting yeast vaults are capable of packaging proteins fused to the INT domain. Furthermore, TEM images show that packaged yeast vaults maintained their integrity and had a morphology was similar to that of empty vaults.

Improved Stability and Catalytic Activities of Yeast Vaults Packaged MnP

Figure 6:
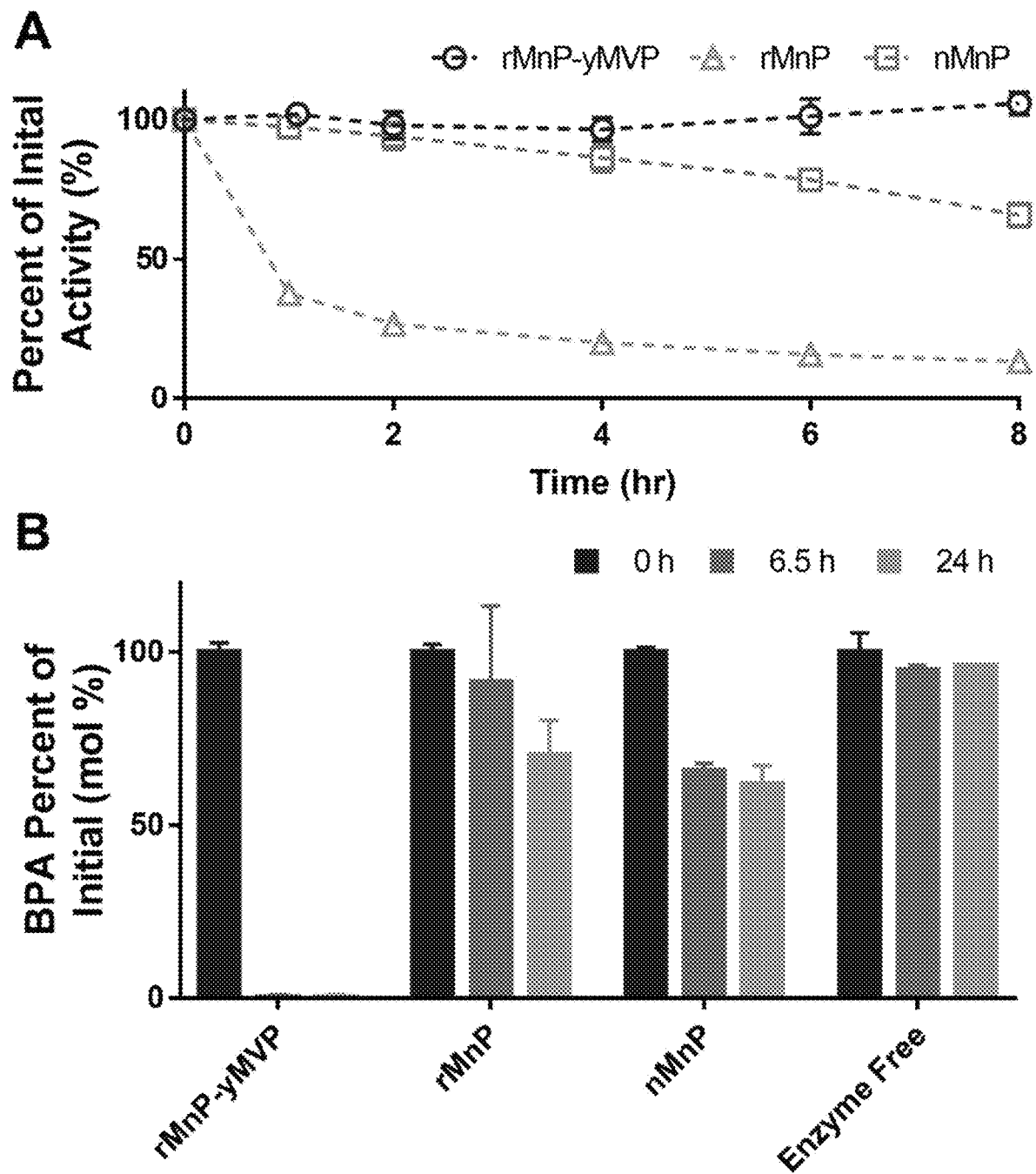
FIG. 6: Improved Stability and Biotransformation Performance of MnP Packaged in Yeast Vaults. Panel A) Thermal stability of different types of MnPs at 25° C. Yeast vaults packaged rMnP maintained its activity over the 8-hour testing period, while unpackaged MnPs experienced significant activity drops. Panel B) Biotransformation of BPA by different MnPs. All enzymes were dosed at 29 U/L initial activity, and samples were collected at 0, 6.5, and 24 hours. In contrast to the slow and incomplete transformation by unpackaged rMnP or nMnP, treatment by rMnP packaged in yeast vaults resulted in nearly complete removal BPA in 6.5 hours. Error bars represent one standard deviation of triplicate samples. The bars for each set from left to right are 0 hours, 6.5 hours, and 24 hours.

Thermal stabilities of MnP encapsulated in yeast vaults and free rMnP and nMnP were compared at 25° C. As shown in FIG. 6, Panel A, the nMnP experienced a continuous activity loss throughout the testing period. After 8 hours incubation, nMnP only maintained 65% of its initial activity. For rMnP, it underwent a faster activity loss than nMnP. One-hour incubation at 25° C. led to 63% activity loss, and only 13% of initial activity was retained after 8 hours incubation, indicating rMnP was less resistant to thermal inactivation than the nMnP. However, following packaging of rMnP in to yeast vaults, its stability was significantly enhanced. The activity of rMnP-yMVP was maintained at 94-105% of its initial activity in the 8-hour testing period, suggesting the rMnP-yMVP did not undergo an activity loss or inactivation at 25° C. in 8 hours. The temperature induced inactivation of enzymes has been attributed to the enzymatic conformational changes, involving tertiary structure disordering, such as break of disulfide bond and ionic interactions, and secondary structure disruption by breaking hydrogen bonds maintaining sub-structures. The enhancement of rMnP activity in yeast vaults is believed to be the result of constraint from vaults shells and surrounding rMnP enzyme molecules. The MVP peptides forming the vaults' shell act like cages, which can hinder the conformation changes of packaged rMnP. Additionally, each vault particle can package multiple copies of rMnP clustered in a limited area adjacent to the waist of the vaults, thus the surrounding rMnP molecules may also contribute to restraining structural changes in rMnP.

BPA, which is widely used in plastic and epoxy resin manufacturing, is one of the major endocrine disruptors found in the environment. Thus, the contaminant biodegradation performance of packaged and unpackaged MnPs using BPA as a model compound was examined. As the least stable MnP, rMnP only removed 30% BPA in 24 hours (FIG. 6, Panel B). For nMnP, the removal rate increased to 39%, however, it was not statistically different from that of rMnP. In contrast, rMnP-yMVP, as the most stable form of MnP, resulted in over 98% removal in 6.5 hours and the residual BPA concentration was below detection limit, which is much more efficient than unpackaged MnPs. Interestingly, although nMnP showed better thermal stability than rMnP, and maintained 78% of its initial activity in 6 hours at 25° C., it did not show statistically higher BPA removal than rMnP, and did not induce significant BPA removal after 6.5 hours. It is possible that the stability of nMnP decreased in reactions due to the inactivation caused by $H_2O_2$, BPA radicals, or the lower pH. But the yeast vaults packaged rMnP still maintained high stability and sustained activity in reactions.

Expression of MVP alone in yeast *P. pastoris* can lead to assembly of intact vault particles. These particles are morphologically similar to endogenous vaults isolated from various eukaryotes. Recombinant yeast vaults maintain the ability to interact with INT-fused components, and can improve the stability and catalytic activity of packaged enzymes. In addition, the formation of vaults on polyribosomes is conserved among eukaryotic species. Since yeasts are one of the simplest cells in eukaryota, the methods of producing vault particles as described herein can be applied to other eukaryotic organisms that lack endogenous vault particles.

As used herein, the terms "vault" and "vault particle" are used interchangeably to refer to a ribonucleoprotein (RNP) comprising complexes of MVPs, alone or in combination with VPARP proteins and/or TEP1 proteins. Vault particles can be naturally occurring or synthetically made. As used herein, "recombinant vaults", "engineered vaults", "recombinant vault particles", and "engineered vault particles" are used interchangeably to refer to vaults that have been synthesized using laboratory techniques, e.g., recombinant methods, as opposed to naturally occurring vaults. In some embodiments, recombinant vaults have a barrel-like shape that is the same as or substantially similar to naturally occurring vaults. In some embodiments, the present invention is directed to yeast vaults. As used herein, "yeast vaults" is used interchangeably with "yMVP vaults" to refer to vault particles that have been recombinantly produced using a yeast host. Yeast vaults according to the present invention may include one or more passenger molecules. The passenger molecules may be carried on the outer surface of the yeast vault and/or packaged within the cavity of the yeast vault.

As used herein, a "major vault protein (MVP)" refers to a protein that has at least about 85%, preferably about 90-100%, more preferably about 95-100%, and most preferably 97-100% sequence identity to a major vault protein and can form a part of a vault. Examples of major vault proteins are provided in the NCBI protein database (available on the Internet, ncbi.nlm.nih.gov/protein) and include GI: 41055865 (rat, NP_073206.2), GI: 239052674 (mouse, NP_542369.2), and GI: 15990478 (human, AAH15623.1, herein referred to as "human MVP" or "hMVP"). In some embodiments, the MVP has at least about 85%, preferably about 90-100%, more preferably about 95-100%, and most preferably 97-100% sequence identity to human MVP. In some embodiments, the MVP has 85%, 86%, 87%, 88%, 89%, 90%, 91%, 92%, 93%, 94%, 95%, 96%, 97%, 98%, 99%, or 100% sequence identity to human MVP. MVPs can be synthetic, mutated, modified, human, animal (e.g., rat MVP), etc. In some embodiments, the MVP is an analog of human MVP. In some embodiments, the MVP is a homolog of human MVP. As used herein, "analogs" refer to proteins (or nucleic acid molecules) of heterologous origins that display the same or substantially similar activity. As used herein, "homologs" refer to proteins (or nucleic acid molecules) of a common origin, but do not necessarily exhibit the same or substantially similar activity.

In some embodiments, the present invention is directed to a yeast MVP (yMVP). As used herein, "yMVPs" refer to any MVP (e.g., human MVP, rat MVP, mouse MVP, monkey MVP, etc.) that has been expressed in a yeast host. In some embodiments, yMVPs according to the present invention are encoded by a codon optimized yMVP cDNA.

As used herein, a "codon optimized yMVP cDNA" refers to a cDNA molecule that encodes an MVP, which cDNA molecule has been codon optimized for expression in a given host cell, e.g., a yeast host cell. In some embodiments, the codon optimized yMVP cDNA has 85%, 86%, 87%, 88%, 89%, 90%, 91%, 92%, 93%, 94%, 95%, 96%, 97%, 98%, 99%, or 100% sequence identity to (SEQ ID NO: 1)
ATGGCAACAGAGGAGTTTATTATCAGAATCCCACCTTATCACTATATCCA

CGTTTTGGACCAGAACAGTAATGTCTCAAGAGTCGAAGTTGGTCCAAAGA

CTTACATCAGACAAGATAACGAAAGAGTTTTGTTCGCTCCTATGAGAATG

GTTACTGTTCCACCTAGACATTATTGTACTGTTGCTAATCCAGTTTCCAG

AGATGCTCAAGGTTTGGTTTTGTTTGATGTTACTGGTCAAGTTAGATTGA

GACACGCTGATTTGGAAATTAGATTGGCTCAAGATCCATTCCCTTTGTAC

CCTGGTGAAGTTTTGGAAAAGGATATTACTCCATTGCAAGTTGTTTTGCC

TAACACTGCTTTGCATTTGAAGGCTTTGTTGGATTTTGAGGATAAGGATG

GAGATAAAGTTGTTGCTGGAGATGAGTGGTTGTTCGAAGGTCCAGGTACT

TATATTCCTAGAAAGGAAGTTGAGGTTGTTGAAATCATCCAAGCTACTAT

CATCAGACAAAACCAGGCTTTGAGATTGAGAGCTAGAAAGGAGTGTTGGG

ATAGAGATGGTAAAGAAAGAGTTACTGGTGAAGAGTGGTTGGTTACTACT

GTTGGTGCTTACTTGCCAGCTGTTTTCGAAGAGGTTTTGGATTTGGTTGA

TGCTGTTATTTTGACTGAAAAGACTGCTTTGCATTTGAGAGCTAGAAGAA

ACTTTAGAGATTTCAGAGGTGTTTCCAGAAGAACCGGAGAGGAATGGTTG

GTTACTGTTCAAGATACTGAAGCTCATGTTCCTGATGTTCACGAAGAGGT

TTTGGGTGTTGTTCCAATTACTACTTTGGGTCCTCACAACTATTGTGTTA

TTTTGGACCCAGTTGGTCCTGATGGTAAAAACCAATTGGGTCAAAAGAGA

GTTGTTAAGGGTGAAAAGTCTTTCTTTTTGCAACCAGGTGAACAATTGGA

ACAAGGTATTCAAGATGTTTACGTTTTGTCTGAGCAACAAGGTTTGTTGT

TGAGAGCTTTGCAACCTTTGGAAGAGGGTGAAGATGAAGAGAAGGTTTCT

CATCAAGCTGGAGATCATTGGTTGATTAGAGGTCCATTGGAGTATGTTCC

TTCTGCTAAAGTTGAAGTTGTTGAAGAGAGACAAGCTATTCCATTGGATG

AAAACGAGGGTATCTACGTTCAAGATGTTAAGACTGGTAAAGTTAGAGCT

GTTATTGGTTCTACTTATATGTTGACTCAAGATGAGGTTTTGTGGGAAAA

GGAGTTGCCACCTGGTGTTGAAGAGTTGTTGAACAAGGGTCAAGATCCAT

TGGCTGATAGAGGTGAAAAGGATACTGCTAAATCTTTGCAACCATTGGCT

CCTAGAAACAAGACTAGAGTTGTTTCTTACAGAGTTCCTCATAATGCTGC

TGTTCAAGTTTACGATTATAGAGAGAAAAGAGCTAGAGTTGTTTTTGGTC

CAGAATTGGTTTCTTTGGGTCCTGAAGAGCAATTCACTGTTTTGTCTTTG

TCTGCTGGTAGACCAAAAAGACCACATGCTAGAAGAGCTTTGTGTTTGTT

GTTGGGTCCAGATTTCTTTACTGATGTTATCACTATCGAAACTGCTGATC

ATGCTAGATTGCAATTGCAATTGGCTTATAACTGGCACTTTGAGGTTAAT

GATAGAAAAGATCCACAAGAAACTGCTAAATTGTTTTCTGTTCCTGATTT

CGTTGGAGATGCTTGTAAAGCTATTGCTTCCAGAGTTAGAGGTGCTGTTG

CTTCTGTTACTTTCGATGATTTCCATAAGAACTCTGCTAGAATCATCAGA

ACTGCTGTTTTCGGTTTCGAGACTTCTGAAGCTAAAGGTCCAGATGGTAT

GGCTTTGCCAAGACCTAGAGATCAAGCTGTTTTCCCTCAAAACGGTTTGG

TTGTTTCTTCTGTTGATGTTCAATCTGTTGAGCCAGTTGATCAAAGAACT

AGAGATGCTTTGCAAAGATCTGTTCAATTGGCTATCGAAATCACTACTAA

TTCTCAAGAGGCTGCTGCTAAGCACGAAGCTCAAAGATTGGAACAAGAGG

CTAGAGGTAGATTGGAAAGACAAAAGATTTTGGATCAATCTGAAGCTGAG

AAGGCTAGAAAAGAGTTGTTGGAATTGGAGGCTTTGTCTATGGCTGTTGA

ATCTACTGGTACTGCTAAGGCTGAAGCTGAGTCCAGAGCTGAAGCTGCTA

GAATTGAAGGAGAGGGTTCTGTTTTGCAGGCTAAGTTGAAAGCTCAGGCT

TTGGCTATTGAAACTGAGGCTGAATTGCAAAGAGTTCAAAAAGTTAGAGA

GTTGGAATTGGTTTACGCTAGAGCCCAATTGGAGTTGGAAGTTTCTAAGG

CTCAACAATTGGCTGAGGTTGAAGTTAAGAAGTTTAAGCAAATGACTGAG

GCTATTGGTCCATCTACTATTAGAGATTTGGCTGTTGCTGGTCCTGAAAT

GCAGGTTAAGTTGTTGCAATCTTTGGGTTTGAAATCTACTTTGATCACTG

ATGGTTCTACTCCAATTAACTTGTTTAATACTGCTTTCGGTTTGTTGGGT

ATGGGTCCAGAGGGTCAACCTTTGGGTAGAAGAGTTGCTTCTGGTCCATC

TCCTGGTGAAGGTATTTCTCCACAGTCAGCCCAAGCACCTCAAGCACCAG

GAGATAATCATGTCGTTCCAGTTCTTAGA which encodes human MVP (SEQ ID NO: 2, AAH15623.1).

As used herein, a "VPARP protein" refers to a protein that has at least about 85%, preferably about 90-100%, more preferably about 95-100%, and most preferably 97-100% sequence identity to a vault poly ADP-ribose polymerase and can form a part of a vault. Examples of VPARP proteins are provided in the NCBI protein database (available on the Internet, ncbi.nlm.nih.gov/protein) and include GI: 149064059 (rat, EDM14329.1), GI: 281485553 (mouse, NP_001139450.2), and GI: 112789550 (human, NP_006428.2). In some embodiments, the VPARP protein has at least about 85%, preferably about 90-100%, more preferably about 95-100%, and most preferably 97-100% sequence identity to human VPARP protein. VPARP proteins can be synthetic, mutated, modified, human, animal (e.g., rat VPARP protein), etc. In some embodiments, the VPARP protein is an analog of human VPARP protein. In some embodiments, the VPARP protein is a homolog of human VPARP protein. As used herein, an "mINT sequence", "mINT", and "INT" are used interchangeably to refer to a major vault protein interaction domain (mINT, also referred to as the "minimal interaction domain") of a given VPARP protein. In some embodiments, the mINT sequence comprises or consists of amino acid residues 1563-1726 of a given VPARP protein, e.g., human VPARP. In some embodiments, the mINT sequence comprises or consists of amino acid residues 1563-1709 of a given VPARP protein, e.g., human VPARP.

As used herein, a "TEP1 protein" refers to a protein that has 90-100%, preferably 95-100%, sequence identity to a telomerase/vault associated protein 1 and can form part of a vault. Examples of TEP1 proteins are provided in the NCBI protein database (available on the Internet, ncbi.nlm.nih.gov/protein) and include GI: 12018250 (rat, NP_072113.1), GI: 6678285 (mouse, NP_033377.1), and GI: 21536371 (human, NP_009041.2). TEP1 proteins can be synthetic, mutated, modified, human, animal (e.g., rat TEP1), etc.

As used herein, "passenger molecules" refer to molecules of interest that are carried on the surface of vault particles, molecules enclosed in vault particles (e.g., when vault particles are fully closed), molecules contained within the cavities of vault particles (e.g., when vault particles have openings or are partially formed), and molecules incorporated in the structures of vaults (e.g., covalently attached to the MVPs of vaults). In some embodiments, the passenger molecule is a protein (or fragment thereof), which is referred to herein as a "passenger peptide" or "passenger protein". In some embodiments, the passenger molecule is heterologous to its carrier molecule (e.g., heterologous to the vault particle containing the passenger molecule, heterologous to the mINT sequence or MVP that the passenger molecule is covalently attached to, etc.). In some embodiments, the passenger molecule is covalently linked to its carrier molecule using methods, e.g., recombinant techniques, in the art. In some embodiments, the passenger molecule is covalently linked to its carrier molecule using a linker, e.g., a flexible amino acid linker, in the art. In some embodiments, one or more passenger molecules are attached directly or indirectly (e.g., via a linker or an mINT sequence) to the outside, the inside, or both the outside and inside of a vault particle. In some embodiments, the covalent link between a given passenger molecule and a given mINT sequence or a given MVP is by way of chemical modification and/or protein coupling methods in the art. See, e.g., Benner, et al. (2017) ACS Nano 11: 872-881. In some embodiments, where multiple passenger molecules (which may be the same or different) are attached to a vault particle, the manner in which the multiple passenger molecules are attached may be the same or different, e.g., some passenger molecules may be indirectly attached to the vault particle by way of an mINT sequence, while other passenger molecules are covalently attached to the N-terminus, the C-terminus, or both the N- and C-terminus of the MVP forming the vault particle.

As used herein, an "mINT passenger molecule" refers to a passenger molecule that is covalently linked to an mINT sequence.

As used herein, an "N-linked passenger molecule" refers to a passenger molecule that is covalently linked to the N-terminus of an MVP, which may or may not be a yMVP.

As used herein, an "C-linked passenger molecule" refers to a passenger molecule that is covalently linked to the C-terminus of an MVP, which may or may not be a yMVP.

As used herein, "mINT fusion packaging" refers to a method where one or more mINT passenger molecules are mixed with formed vaults to thereby package the fusion molecules in the interior cavities of vaults (e.g., US 20120213809).

As used herein, "passive packaging" refers to a method where one or more passenger molecules are mixed with MVPs as they are being folded into vault structures having an interior cavity (e.g., WO 2016/049122). As used herein, "passively packaged passenger molecules" refer to a passenger molecule that has been packaged in the interior cavity of a vault particle by passive packaging.

As used herein, a "yeast host" refers to a microorganism belonging to Ascomycota division of the Kingdom Fungi. In some embodiments, the yeast host is a microorganism belonging to the subdivision Saccharomycotina. In some embodiments, the yeast host is a microorganism belonging to the order Saccharomycetales. In some embodiments, the yeast host is a microorganism belonging to the family Saccharomycetaceae. In some embodiments, the yeast host is a microorganism belonging to the genus *Pichia*. In some embodiments, the yeast host is a microorganism belonging to the genus *Saccharomyces*. In some embodiments, the yeast host is *Saccharomyces cerevisiae*. In some embodiments, the yeast host is *Pichia pastoris*.

In some embodiments, the yeast host belongs to the genus *Brettanomyces, Candida, Citeromyces, Cyniclomyces, Debaryomyces, Issatchenkia, Kazachstania* (synonymous with Arxiozyma), *Kluyveromyces, Komagataella, Kuraishia, Lachancea, Lodderomyces, Nakaseomyces, Pachysolen, Pichia, Saccharomyces, Spathaspora, Tetrapisispora, Vanderwaltozyma, Torulaspora, Williopsis, Zygosaccharomyces*, or *Zygotorulaspora*. In some embodiments, the yeast host belongs to the genus *Brettanomyces, Candida, Kazachstania* (synonymous with Arxiozyma), *Kluyveromyces, Komagataella, Kuraishia, Lachancea, Nakaseomyces, Pichia, Saccharomyces, Spathaspora, Tetrapisispora, Vanderwaltozyma, Torulaspora, Zygosaccharomyces*, or *Zygotorulaspora*. In some embodiments, the yeast host belongs to the genus *Pichia* or *Saccharomyces*.

In some embodiments, the yeast host belongs to the species *P. farinosa, P. anomala, P. heedii, P. guilliermondii, P. kluyveri, P. membranifaciens, P. norvegensis, P. ohmeri, P. pastoris, P. methanolica,* or *P. subpelliculosa*. In some embodiments, the yeast host belongs to the species *P. pastoris*.

In some embodiments, the yeast host belongs to the species *S. arboricolus, S. bayanus, S. boulardii, S. bulderi, S. cariocanus, S. cariocus, S. cerevisiae, S. chevalieri, S. dairenensis, S. elhpsoideus, S. eubayanus, S. exiguus, S. florentinus, S. fragilis, S. kluyveri, S. kudriavzevii, S. martiniae, S. mikatae, S. monacensis, S. norbensis, S. paradoxus, S. pastorianus, S. spencerorum, S. turicensis, S. unisporus, S. uvarum,* or *S. zonatus*. In some embodiments, the yeast host belongs to the species *S. cerevisiae*. In some embodiments, the yeast host is a fission yeast such as *Schizosaccharomyces pombe*.

In some embodiments, the host organism used to produce vault particles is a filamentous fungal host such as *Trichoderma reesei, Aspergillus niger, Aspergillus oryzae*, and the like. See, e.g., Meyer (2008) Biotechnol Adv 26(2):177-85.

In some embodiments, the host cells are cultured under conditions suitable for a given MVP or formation of a given vault particle. Conditions suitable for expression of a given MVP or formation of a given vault particle in a host cell are conditions (time, temperature, nutrients, etc.) under which the host cells are capable of growing and propagating until reaching a stationary growth phase and, if an inducible promoter is used to control the expression of the nucleic acid molecule that encodes the given MVP, the conditions include the presence of the agent that activates the inducible promoter.

In some embodiments, the present invention is directed to yeast vaults. In some embodiments, the present invention is directed to yMVPs. In some embodiments, the present invention is directed to codon optimized yMVP cDNAs.

As used herein, a given percentage of "sequence identity" refers to the percentage of nucleotides or amino acid residues that are the same between sequences, when compared and optimally aligned for maximum correspondence over a given comparison window, as measured by visual inspection or by a sequence comparison algorithm in the art, such as the BLAST algorithm, which is described in Altschul et al., J. Mol. Biol. 215:403-410 (1990). Software for performing BLAST (e.g., BLASTP and BLASTN) analyses is publicly available through the National Center for Biotechnology Information (ncbi.nlm.nih.gov). The comparison window can exist over a given portion, e.g., a functional domain, or an arbitrarily selection a given number of contiguous nucleotides or amino acid residues of one or both sequences.

Alternatively, the comparison window can exist over the full length of the sequences being compared. For purposes herein, where a given comparison window (e.g., over 80% of the given sequence) is not provided, the recited sequence identity is over 100% of the given sequence. Additionally, for the percentages of sequence identity of proteins provided herein, the percentages are determined using BLASTP 2.8.0+, scoring matrix BLOSUM62, and the default parameters available at blast.ncbi.nlm.nih.gov/Blast.cgi. See also Altschul, et al. (1997), Nucleic Acids Res. 25:3389-3402; and Altschul, et al. (2005) FEBS J. 272:5101-5109.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BEST-FIT, FASTA, and TFASTA in the Wisconsin Genetics Software Package, Genetics Computer Group, 575 Science Dr., Madison, Wis.), or by visual inspection.

As used herein, the terms "protein", "polypeptide" and "peptide" are used interchangeably to refer to two or more amino acids linked together. Groups or strings of amino acid abbreviations are used to represent peptides. Except when specifically indicated, peptides are indicated with the N-terminus on the left and the sequence is written from the N-terminus to the C-terminus.

As used herein, an "isolated" compound refers to a compound that is isolated from its native environment. For example, an isolated polynucleotide is one that does not have the bases normally flanking the 5' end and/or the 3' end of the polynucleotide as it is found in nature. As another example, an isolated polypeptide is one that does not have its native amino acids, which correspond to the full-length polypeptide, flanking the N-terminus, C-terminus, or both.

In some embodiments, the yeast vaults, yMVP, and codon optimized yMVP cDNAs of the present invention are substantially purified. As used herein, a "substantially purified" compound refers to a compound that is removed from its natural environment and/or is at least about 60% free, preferably about 75% free, and more preferably about 90% free, and most preferably about 95-100% free from other macromolecular components or compounds with which the compound is associated with in nature or from its synthesis.

Compositions of the present invention, including pharmaceutical compositions and vaccines, include one or more yeast vaults, one or more yMVPs, and/or one or more codon optimized yMVP cDNAs. In some embodiments, a composition of the present invention comprises, consists essentially of, or consists of one or more yeast vaults and/or one or more yMVPs. In some embodiments, the composition is a crude homogenate that comprises one or more yeast vaults.

As used herein, the phrase "consists essentially of" in the context of, e.g., a yeast vault, means that the composition may comprise other ingredients, but does not comprise vault particles that are not yeast vaults.

The term "pharmaceutical composition" refers to a composition suitable for pharmaceutical use in a subject. A pharmaceutical composition generally comprises an effective amount of an active agent, e.g., one or more yeast vaults according to the present invention, and a pharmaceutically acceptable carrier. The term "effective amount" refers to a dosage or amount sufficient to produce a desired result. The desired result may comprise an objective or subjective improvement in the recipient of the dosage or amount, e.g., long-term survival, effective prevention of a disease state, and the like.

One or more yeast vaults according to the present invention may be administered, preferably in the form of pharmaceutical compositions, to a subject. Preferably the subject is mammalian, more preferably, the subject is human. Preferred pharmaceutical compositions are those comprising at least one yeast vault in a therapeutically effective amount or an immunogenic amount, and a pharmaceutically acceptable vehicle.

Vaccines according to the present invention provide a protective immune response when administered to a subject. As used herein, a "vaccine" according to the present invention is a pharmaceutical composition that comprises an immunogenic amount of at least one yeast vault and provides a protective immune response when administered to a subject. The protective immune response may be complete or partial, e.g., a reduction in symptoms as compared with an unvaccinated subject.

As used herein, an "immunogenic amount" is an amount that is sufficient to elicit an immune response in a subject and depends on a variety of factors such as the immunogenicity of the given yeast vault, the manner of administration, the general state of health of the subject, and the like. The typical immunogenic amounts for initial and boosting immunizations for therapeutic or prophylactic administration may range from about 120 µg to 8 mg per kilogram of body weight of a subject. For example, the typical immunogenic amount for initial and boosting immunization for therapeutic or prophylactic administration for a human subject of 70 kg body weight ranges from about 8.4 mg to about 560 mg, preferably about 10-100 mg, more preferably about 10-20 mg, per about 65-70 kg body weight of a subject. Examples of suitable immunization protocols include an initial immunization injection (time 0), followed by booster injections at 4, and/or 8 weeks, which these initial immunization injections may be followed by further booster injections at 1 or 2 years if needed.

As used herein, a "therapeutically effective amount" refers to an amount that may be used to treat, prevent, or inhibit a given disease or condition in a subject as compared to a control. Again, the skilled artisan will appreciate that certain factors may influence the amount required to effectively treat a subject, including the given disease or disorder and degree thereof, previous treatments, the general health and age of the subject, and the like. Nevertheless, therapeutically effective amounts may be readily determined by methods in the art. It should be noted that treatment of a subject with a therapeutically effective amount or an immunogenic amount may be administered as a single dose or as a series of several doses. The dosages used for treatment may increase or decrease over the course of a given treatment. Optimal dosages for a given set of conditions may be ascertained by those skilled in the art using dosage-determination tests and/or diagnostic assays in the art. Dosage-determination tests and/or diagnostic assays may be used to monitor and adjust dosages during the course of treatment.

The compositions of the present invention may include an adjuvant. As used herein, an "adjuvant" refers to any substance which, when administered in conjunction with (e.g., before, during, or after) a pharmaceutically active agent, such as a yeast vault according to the present invention, aids the pharmaceutically active agent in its mechanism of action. Thus, an adjuvant in a vaccine according to the present invention is a substance that aids the at least one yeast vault in eliciting an immune response. Suitable adjuvants include incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, nor-MDP), N-acetylmuramyl-L-alanyl-D-isoglutaminyl-L-alanine-2-(1'-2'-dipa-lmitoyl-sn-glycero-3-hydroxyphosphoryloxy)-ethylamine (CGP 19835A, MTP-PE), and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by methods in the art.

Pharmaceutical compositions of the present invention may be formulated for the intended route of delivery, including intravenous, intramuscular, intra peritoneal, subcutaneous, intraocular, intrathecal, intraarticular, intrasynovial, cisternal, intrahepatic, intralesional injection, intracranial injection, infusion, and/or inhaled routes of administration using methods known in the art. Pharmaceutical compositions according to the present invention may include one or more of the following: pH buffered solutions, adjuvants (e.g., preservatives, wetting agents, emulsifying agents, and dispersing agents), liposomal formulations, nanoparticles, dispersions, suspensions, or emulsions, as well as sterile powders for reconstitution into sterile injectable solutions or dispersions. The compositions and formulations of the present invention may be optimized for increased stability and efficacy using methods in the art. See, e.g., Carra et al. (2007) Vaccine 25:4149-4158.

The compositions of the present invention may be administered to a subject by any suitable route including oral, transdermal, subcutaneous, intranasal, inhalation, intramuscular, and intravascular administration. It will be appreciated that the preferred route of administration and pharmaceutical formulation will vary with the condition and age of the subject, the nature of the condition to be treated, the therapeutic effect desired, and the particular yeast vault used.

As used herein, a "pharmaceutically acceptable vehicle" or "pharmaceutically acceptable carrier" are used interchangeably and refer to solvents, dispersion media, coatings, antibacterial and antifungal agents, isotonic and absorption delaying agents, and the like, that are compatible with pharmaceutical administration and comply with the applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. Pharmaceutically acceptable vehicles include those known in the art. See, e.g., REMINGTON: THE SCIENCE AND PRACTICE OF PHARMACY. $20^{th}$ ed. (2000) Lippincott Williams & Wilkins. Baltimore, Md., which is herein incorporated by reference.

The pharmaceutical compositions of the present invention may be provided in dosage unit forms. As used herein, a "dosage unit form" refers to physically discrete units suited as unitary dosages for the subject to be treated; each unit containing a predetermined quantity of the one or more yeast vault calculated to produce the desired therapeutic effect in association with the required pharmaceutically acceptable carrier. The specification for the dosage unit forms of the invention are dictated by and directly dependent on the unique characteristics of the given yeast vault and desired therapeutic effect to be achieved, and the limitations inherent in the art of compounding such an active compound for the treatment of individuals.

Toxicity and therapeutic efficacy of yeast vaults according to the instant invention and compositions thereof can be determined using cell cultures and/or experimental animals and pharmaceutical procedures in the art. For example, one may determine the lethal dose, $LC_{50}$ (the dose expressed as concentration×exposure time that is lethal to 50% of the population) or the $LD_{50}$ (the dose lethal to 50% of the population), and the $ED_{50}$ (the dose therapeutically effective in 50% of the population) by methods in the art. The dose ratio between toxic and therapeutic effects is the therapeutic index and it can be expressed as the ratio $LD_{50}/ED_{50}$. Yeast vaults which exhibit large therapeutic indices are preferred. While yeast vaults that result in toxic side-effects may be used, care should be taken to design a delivery system that targets such compounds to the site of treatment to minimize potential damage to uninfected cells and, thereby, reduce side-effects.

The data obtained from the cell culture assays and animal studies can be used in formulating a range of dosages for use in humans. Preferred dosages provide a range of circulating concentrations that include the $ED_{50}$ with little or no toxicity. The dosage may vary depending upon the dosage form employed and the route of administration utilized. Therapeutically effective amounts and dosages of one or more yeast vaults according to the present invention can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Additionally, a dosage suitable for a given subject can be determined by an attending physician or qualified medical practitioner, based on various clinical factors.

In some embodiments, the present invention is directed to kits which comprise one or more yeast vaults, optionally in a composition, packaged together with one or more reagents or drug delivery devices for preventing, inhibiting, reducing, or treating a given disease or disorder in a subject. Such kits include a carrier, package, or container that may be compartmentalized to receive one or more containers, such as vials, tubes, and the like. In some embodiments, the kits optionally include an identifying description or label or instructions relating to its use. In some embodiments, the kits comprise the one or more yeast vaults, optionally in one or more unit dosage forms, packaged together as a pack and/or in drug delivery device, e.g., a pre-filled syringe. In some embodiments, the kits include information prescribed by a governmental agency that regulates the manufacture, use, or sale of compounds and compositions according to the present invention.

The following examples are intended to illustrate but not to limit the invention.

Material and Methods

Plasmid Subcloning, Yeast Transformation, and Protein Expression

The human MVP coding sequence was subcloned downstream of the $P_{GAP}$ promoter in the yeast vector pGAPZA (Invitrogen, CA) into the EcoRI and KpnI sites to generate the yeast expression vector yMVP-pGAPZA. Afterwards, the plasmid was linearized with BspHI, and transformed into P. pastoris protease deficient strain SMD1168 using the GenePulser electroporator (Bio-Rad Labs, CA) using methods in the art. Electroporation was performed at 1.5 kV, 200Ω, and 25 µF by a single pulse. The transformation mixture was plated on YPDS agar containing 100 µg/mL of the antibiotic ZEOCIN. ZEOCIN resistant transformants were selected and re-streaked on new YPD plates containing ZEOCIN to select single colonies. Positive colonies were inoculated into 3 mL of YPD medium with 100 µg/mL ZEOCIN and cultured at 30° C. and 200 rpm overnight, which were then used to inoculate 500 mL YPD medium to an OD600 of 0.03. The cultures were maintained at 30° C., 200 rpm for 30 hours. Cells were harvested in a pre-weighted 50 mL tube by centrifuging at 3000×g for 5 minutes at 4° C., and washed with 10 mL DI water. Cell pellets were weighted and stored at −80° C.

Preparation of Vault Particles from Yeast Cells

Each gram of yMVP cell pellet was resuspended in 3 mL of breaking buffer (50 mM sodium phosphate, pH 7.4, 1 mM EDTA, and 5% glycerol) containing 1 mM dithiothreitol (DTT), 1 mM phenylmethylsulfonyl fluoride (PMSF), and 50 µL of protease inhibitor (PI) cocktail (Sigma-Aldrich, MO). Cells lysis was performed by vortexing with 4 mL of glass beads (0.5 mm diameter). The lysate was collected and centrifuged at 20,000×g for 20 minutes at 4° C. to separate unbroken cells, cell debris, and insoluble cell fractions (P20). Vault particles in the clarified supernatant (S20) were then purified following the standard vault purification protocol using methods in the art. Briefly, the S20 was centrifuged at 100,000×g for 1 hour at 4° C. to collect vault particles and other macro-complexes in the pellet (P100). The supernatant (S100) was also saved for analysis. Subsequently, P100 was homogenized in 3.5 mL Buffer A (50 mm Tris-HCl pH 7.4, 75 mM NaCl, 0.5 mM $MgCl_2$) containing 1% Triton X-100, 1 mM DTT and 35 µL of PI cocktail by douncing 20 times. Vaults were precipitated with salt, followed by centrifugation at 20,000×g for 15 minutes at 4° C. The pellet was resuspended in 1.5 mL Buffer A and loaded onto a discontinuous sucrose gradient (20, 30, 40, 45, 50, 60% sucrose layers), and spun at 78,000×g for 16 hours using slow acceleration and deceleration programs. Each layer was collected and diluted in 5 volumes of Buffer A, and centrifuged for 2 hours at 100,000×g to produce a pellet ("100,000×g pellet"). The pellets were resuspended in 500 µL Buffer A and analyzed on SDS-PAGE followed by either Coomassie staining or Western blotting.

Purification of Vault Particle Preparations

Methods in the art may be used to further purify vault particle preparations. Generally, after a host cell is induced to express vault particles, the host cell is disrupted using methods in the art, and the vault particles expressed by the host cell are isolated or purified by, e.g., differential centrifugation, density gradient centrifugation filtration (ultra, depth, etc.), precipitation and differential solubilization, free-flow electrophoresis, chromatography (size exclusion, gel filtration, affinity, ion exchange, hydrophobic, gravity, HPLC, FPLC, etc.), or the like.

As an example, 100,000×g pellets as produced above were resuspended in 4.5 volumes of lysis buffer (Buffer A containing 1% Triton X-100) based on the original wet pellet weight (e.g., if 1 g wet pellet weight, the pellet was resuspended in 4.5 ml lysis buffer). After addition of the lysis buffer, the pellets were completely resuspended by dounce homogenizing 10-20 times. Solid ammonium acetate (mw 77.08 g) was added and gently mixed to give a 1M final concentration. The mixture was incubated on a rotator at 4° C. for 20 minutes and then spun for 10 minutes at 13,000×g at 4° C. The resulting pellet was resuspended in 1-2 ml of Buffer A (without detergent) per gram of the starting wet pellet weight by douncing 10-20 times to complete resuspension. The suspension was subjected to a TMAE HiCap fractogel (Millipore EMD) column centrifuge at 13,000 g for 10 minutes to remove any aggregates using the following protocol:

Buffer A: 50 mM Tris-Cl, pH 7.5, 75 mM NaCl, 0.5 mM $MgCl_2$

Buffer B: 50 mM Tris-Cl, pH 7.5, 1 M NaCl, 0.5 mM $MgCl_2$

Fraction size: 1CV

1) Pre-equilibrate column with 3 CV of Buffer A, then 2 CV Buffer B and then 3CV Buffer A at 2.5 ml/min flow rate.
2) Inject Sample (2-3 CV) at a flow rate of 1 ml/min. Adjust the salt concentration of the sample to be at or below 75 mM.
3) Wash unbound sample with 8-10 CV of Buffer A at 95% and Buffer B at 5% (verify that the UV280 has reached baseline) at 2.5 ml/min flow rate.
4) Elute protein using a 20-30 CV linear salt gradient with a starting concentration of Buffer A at 95% and Buffer B at 5%, final concentration of Buffer B at 100%. Run at a flow rate of 2.5 ml/min flow rate. Vaults typically elute at about 0.2 M NaCl, across 3-5 fractions.
5) Regenerate column with 2 CV Buffer B and then 3 CV Buffer A at 2.5 ml/min flow rate. The column is preferably deep cleaned using 2.5 M NaCl and 0.5 N NaOH in order to remove protein and any nucleic acid contaminants. Wash thoroughly with water and finally store column in 20% ethanol.

Quantification of yMVP

Concentrations of yMVP in S20, S100, and salt precipitated fractions were quantified by an enzyme-linked immunoabsorbent assay (ELISA) using purified insect cell produced human MVP (hMVP) as the standard. Masses of yMVP in P100 were calculated by subtracting yMVP in S100 from it in S20. One-hundred microliter of serially diluted yMVP samples and hMVP standards were added to 96-well ELISA plates in triplicates and incubated at 4° C. overnight. After removing unbound material, plates were blocked with 100 µL of 5% (v/v) normal goat serum (NGS) in PBS containing 0.05% (v/v) Tween 20 (PBST) at room temperature for 1 hour, and washed three times with 200 µL/well of PBST before addition of 100 µL/well of anti-MVP polyclonal antibody in PBST containing 5% (v/v) NGS. Plates were incubated with the primary antibody at room temperature for 1 hour, and washed three times with 200 µL/well of PBST. One-hundred microliter of 1:2000 diluted HRP-conjugated goat anti-rabbit IgG antibody (Bio-Rad, CA) in PBST with 5% (v/v) NGS was then added to each well. After 1-hour incubation at room temperature, followed by three washes with 200 µL/well of PBST, 100 µL of TMB+ substrate-chromogen solution (Agilent Dako, Calif.) was added to each well. Reactions were maintained for 10-30 minutes, and stopped by adding 100 of 1 N $H_2SO_4$ per well. OD at 450 nm was recorded and used for calculating yMVP concentrations.

Packaging of INT-Fused Protein into Yeast Vaults

Fluorescent protein mCherry was chosen to test the packaging ability of yeast vaults. Cells expressing mCherry fused to INT (mCherry-INT) were lysed with yMVP cell pellets as described above. Lysates were incubated on ice for 30 minutes before the first centrifugation. Yeast vaults packaged with mCherry-INT were isolated following the vault purification procedure described above.

Characterization of Yeast Vaults

Purified vaults were examined by negative staining TEM to evaluate their size, morphology and dispersion. Samples were absorbed on carbon-coated copper EM grids by floating the grids on 20 µL vault solution for 5 minutes at room temperature. The grids were then blotted on a filter paper and stained by floating on 1 mL of 1% uranyl acetate (UA) aqueous solution for 5 minutes. Extra UA solution was blotted on a filter paper, and the grid was air dried prior to viewing in a TEM (JEOL 1200EX). Phase analysis light scattering (PALS) was used to determine the zeta potential of purified vault particles.

Evaluation of Yeast Vaults Packaged MnP

INT fused MnP (rMnP) was produced in insect Sf9 cells as previously described (Wang et al., 2015). The Sf9 culture infected with rMnP baculoviruses was collected at 72 hours, and spun at 3000×g for 5 minutes at 4° C. to remove cells and cell debris. Baculoviruses and small cell debris were removed from the supernatant by centrifugation at 100,000×g for 1 hour. To obtain rMnP crude extract, the supernatant was concentrated using 30 kDa Amicon Ultra centrifugal filters (Millipore Sigma, MA), and desalted using a PD-10 column (GE Healthcare Bio-Sciences, MA). rMnP was eluted in Buffer A, and passed through a 0.2 µm filter. To make yeast vaults packaged with rMnP (hereafter rMnP-yMVP), purified yeast vaults were added to the virus free rMnP culture supernatant, and mixed at 4° C. for 1 hour. rMnP-yMVP was separated from unpackaged rMnP by 1 hour centrifugation at 100,000×g. Supernatant was decanted, and the rMnP-yMVP pellet was resuspended in buffer A. rMnP and rMnP-yMVP were stored at −20° C. and 4° C. before use, respectively.

Natural MnP (nMnP) was purified from the fungus *Phanerochaete chrysosporium* using methods in the art. In brief, spores were collected from fungus growing on PDA agar, and inoculated to Kirk medium. The liquid culture was maintained at 30° C., 150 rpm with 30 minutes aeration every day. After 5 days incubation, culture supernatant containing nMnP was collected by centrifugation before lignin peroxidase activity appeared, followed by ammonium sulfate precipitation at 80% saturation (4° C.). Precipitates were resuspended in sterile DI water, and centrifuged for 10 minutes at 7800×g at 4° C. to remove insoluble aggregates. The residual ammonium sulfate was removed by running the supernatant through PD-10 desalting columns, and nMnP was eluted in Buffer A. The nMnP eluate was then passed through a 0.2 µm filter, and stored at −20° C. before use.

To compare the thermal stability of MnP enzymes, triplicates of rMnP-yMVP, rMnP and nMnP were incubated at 25° C. MnP enzymatic activities were measured at 0, 1, 2, 4, 6, and 8 hours using 2,2'-azino-bis(3-ethylbenzothiazoline-6-sulphonic acid) (ABTS) oxidation assay, which was performed in pH 4.0 50 mM malonate buffer containing 0.5 mM ABTS, 2 mM $MnCl_2$, MnP samples, and 0.3 mM $H_2O_2$. The formation of oxidized ABTS was monitored by recording the absorbance change at 420 nm, where is the absorption peak of ABTS oxidation product ($\varepsilon_{420\ nm}$=36,000 L $mol^{-1}$ $cm^{-1}$). ABTS oxidation rates were calculated according to stoichiometry of 1 mol of oxidized ABTS produced per 1 mol of ABTS consumed. One unit of MnP is defined as the amount of enzyme required to react 1 µmol/min of substrate. Residual activities at different time points were normalized to their initial activity and plotted against time.

Bisphenol A (BPA) biodegradation tests were conducted in pH 4.5 50 mM malonate buffer containing 150 µM BPA, 1.5 mM $MnCl_2$, 0.3 mM $H_2O_2$, and one MnP (rMnP-yMVP, rMnP, or nMnP) at 25° C. in a shaking incubator (200 rpm). Activities of MnPs were measured in pH 4.5 50 mM malonate buffer with 0.1 mM ABTS, 2 mM $MnCl_2$, and 0.4 mM $H_2O_2$, and dosed at 29 U/L in all reactions. Enzyme free condition, which contained all components except for MnP, was included as a negative control. Triplicate samples were quenched at 0, 6.5, and 24 hours by adding two volumes of methanol, followed by passage through 0.2 µm filters. Residual BPA concentrations were measured using a Hewlett Packard high-performance liquid chromatograph (HP 1050 HPLC system). HPLC separation was carried out with an Agilent C18 column (4.6×250 mm, 5 µm particle size). The mobile phase was operated at 0.5 mL/min, compromising 70% methanol, 30% water, and 0.1% acetic acid. UV detector was monitored at 277 nm.

Co-Expression and Packaging of Passenger Molecules

In some embodiments, a passenger molecule such as a passenger peptide, can be co-expressed with the MVP forming a yeast vault and then packaged therein the yeast vault that is formed. In these embodiments, the passenger molecule and the MVP can be expressed in the same single host cell or in two separate host cells, which may be the same or different.

When expressed in the same single host cell, the nucleic acid molecules encoding the MVP and the passenger molecule can be provided in the same single expression vector or in two separate expression vectors, which may be the same or different. Alternatively, one nucleic acid molecules can be integrated in the host cell's genome while the other is provided in an expression vector or both nucleic acid molecules can be integrated in the host cell's genome at, e.g., two separate locations.

When expressed in the same single host cell, the packaging of the passenger molecule may be by passive packaging or by mINT fusion packaging. Alternatively, the passenger molecule may be packaged on or in the vault particle by expressing it as a C-linked passenger molecule or an N-linked passenger molecule.

When the same single host cell is used to express both the MVP and the passenger molecule, passenger molecules fused to mINT and not fused to mINT may be packaged within the vault particles as they are formed by passive packaging. Additionally, mINT passenger molecules may be packaged within vault particles that are already formed by mINT fusion packaging.

When two separate host cells are used, i.e., one host cell is used to express the MVP and the other host cell is used to express the passenger molecule, the two separate host cells may be cultured in the same or different culture media, e.g., fermentation broth. One host cell may contain one nucleic acid molecule in an expression vector and the other host cell may contain the other nucleic acid molecule integrated into its genome. Alternatively, both host cells can contain the given nucleic acid molecule in an expression vector or both host cells can contain the given nucleic acid molecule integrated in its genome.

When two separate host cells are used, the passenger molecule is preferably an mINT passenger molecule. When one host cell encodes MVP and the other host cell encodes an mINT passenger molecule, the mINT passenger molecule may be packaged into the vault particles by lysing both host cells and mixing the lysates.

The promoters controlling the expression of the nucleic acid molecules encoding the MVP and the passenger molecule, which may be an mINT passenger molecule, can be the same or different. In some embodiments, the promoters are different such that desired expression levels of each can be obtained under, for example, the same fermentation conditions. For example, a constitutively active promoter such as $P_{GAP}$ can be used to provide higher levels of expression of MVP and then an inducible promoter such as $P_{AOX1}$ or, for example, a temperature sensitive promoter, can be used to induce expression of the passenger molecule after a desired amount of MVP has been expressed.

ADDITIONAL EMBODIMENTS

Embodiment 1

A method of making a major vault protein (MVP), which comprises culturing a yeast host containing an expression vector containing a nucleic acid sequence that encodes the major vault protein under the control of a promoter under conditions suitable for expression of the major vault protein.

Embodiment 2

The method according to Embodiment 1, wherein the promoter is a constitutive promoter, an inducible promoter, or a yeast promoter, preferably the promoter is a constitutive promoter.

Embodiment 3

The method according to Embodiment 1, wherein the promoter is PGAP or PAOXI, preferably the promoter is PGAP.

Embodiment 4

The method according to any one of Embodiments 1 to 3, wherein the yeast host is a microorganism belonging to the family Saccharomycetaceae.

Embodiment 5

A method of making a vault particle, which comprises performing the method according to any one of Embodiments 1 to 4 under conditions suitable for formation of the vault particle.

Embodiment 6

The method according to Embodiment 5, and further comprising extracting the vault particle from the yeast host.

Embodiment 7

The method according to any one of Embodiments 1 to 6, and further comprising packaging one or more passenger molecule on or in the vault particle by (a) covalently linking the one or more passenger molecule to the N-terminus and/or C-terminus of the major vault protein, (b) mINT fusion packaging, and/or (c) passive packaging.

Embodiment 8

A composition comprising, consisting essentially of, or consisting of one or more major vault proteins made by the method according to any one of Embodiments 1 to 4 and/or one or more vault particles made by the method according to any one of Embodiments 5 to 7.

The following references are herein incorporated in their entirety:

Afonina, Z. A., Myasnikov, A. G., Shirokov, V. A., Klaholz, B. P., Spirin, A. S., 2014. Conformation transitions of eukaryotic polyribosomes during multi-round translation. Nucleic Acids Res. 43 (1), 618-628.

Aitken, M. D., Irvine, R. L., 1989. Stability testing of ligninase and Mn-peroxidase from *Phanerochaete chrysosporium*. Biotechnol. Bioeng. 34 (10), 1251-1260.

Andersen, D. C.; Krummen, L. Recombinant protein expression for therapeutic applications. Current Opinion in Biotechnology 2002, 13 (2), 117-123.

Baratelli, F.; Takedatsu, H.; Hazra, S.; Peebles, K.; Luo, J.; Kurimoto, P. S.; Zeng, G.; Batra, R. K.; Sharma, S.; Dubinett, S. M.; Lee, J. M. Pre-clinical Characterization of GMP Grade CCL21-Gene Modified Dendritic Cells for Application in a Phase I Trial in Non-Small Cell Lung Cancer. Journal of Translational Medicine 2008, 6.

Benner, N. L., Zang, X., Buehler, D. C., Kickhoefer, V. A., Rome, M. E., Rome, L. H., & Wender, P. A. (2017). Vault Nanoparticles: Chemical Modifications for Imaging and Enhanced Delivery. ACS Nano, 11(1), 872-881.

Berger, W., Steiner, E., Grusch, M., Elbling, L., Micksche, M., 2009. Vaults and the major vault protein: novel roles in signal pathway regulation and immunity. Cell. Mol. Life Sci. 66 (1), 43-61.

Brandes, H. K.; Hartman, F. C.; Lu, T. Y. S.; Larimer, F. W. Efficient expression of the gene for spinach phosphoribulokinase in *Pichia pastoris* and utilization of the recombinant enzyme to explore the role of regulatory cysteinyl residues by site-directed mutagenesis. Journal of Biological Chemistry 1996, 271 (11), 6490-6496.

Brandt, F., Carlson, L.-A., Hard, F. U., Baumeister, W., Grunewald, K., 2010. The three-dimensional organization of polyribosomes in intact human cells. Mol. Cell 39, 560-569.

Buehler, D. C.; Toso, D. B.; Kickhoefer, V. A.; Zhou, Z. H.; Rome, L. H. Vaults Engineered for Hydrophobic Drug Delivery. Small 2011, 7, 1432-1439.

Byrne, M. P.; Smith, T. J.; Montgomery, V. A.; Smith, L. A. Purification, potency, and efficacy of the botulinum neurotoxin type A binding domain from *Pichia pastoris* as a recombinant vaccine candidate. Infection and Immunity 1998, 66 (10), 4817-4822.

Champion, C. I.; Kickhoefer, V. A.; Liu, G.; Moniz, R. J.; Freed, A. S.; Bergmann, L. L.; Vaccari, D.; Raval-Fernandes, S.; Chan, A. M.; Rome, L. H.; Kelly, K. A. A Vault Nanoparticle Vaccine Induces Protective Mucosal Immunity. PLoS ONE 2009, 4 (4).

Chen, Y. C., Shu, L., Qiu, Z. Q., Lee, D. Y., Settle, S. J., Hee, S. Q., Telesca, D., Yang, X., Allard, P., 2016. Exposure to the BPA-substitute bisphenol S causes unique alterations of germline function. PLoS Genet. 12 (7), e1006223.

Clare, J. J.; Rayment, F. B.; Ballantine, S. P.; Sreekrishna, K.; Romanos, M. A. High-Level Expression of Tetanus Toxin Fragment-C in *Pichia-Pastoris* Strains Containing Multiple Tandem Integrations of the Gene. Bio-Technology 1991, 9 (5), 455-460.

Cregg, J. M.; Cereghino, J. L.; Shi, J. Y.; Higgins, D. R. Recombinant protein expression in *Pichia pastoris*. Molecular Biotechnology 2000, 16 (1), 23-52.

Eibes, G., Cajthaml, T., Moreira, M. T., Feijoo, G., Lema, J. M., 2006. Enzymatic degradation of anthracene, dibenzothiophene and pyrene by manganese peroxidase in media containing acetone. Chemosphere 64 (3), 408-414.

Esposito, A. M., Mateyak, M., He, D., Lewis, M., Sasikumar, A. N., Hutton, J., Copeland, P. R., Kinzy, T. G., 2010. Eukaryotic polyribosome profile analysis. J. Visualized Exp. (40), e1948.

Fahnestock, S. R.; Bedzyk, L. A. Production of synthetic spider dragline silk protein in *Pichia pastoris*. Applied Microbiology and Biotechnology 1997, 47 (1), 33-39.

Fernandez, J. M.; Hoeffler, J. P., Gene expression systems: using nature for the art of expression. Academic Press: 1998.

Gerngross, T. U. Advances in the production of human therapeutic proteins in yeasts and filamentous fungi. Nature Biotechnology 2004, 22 (11), 1409-1414.

Gu, L.; Lajoie, C.; Kelly, C. Expression of a *Phanerochaete chrysosporium* manganese peroxidase gene in the yeast *Pichia pastoris*. Biotechnology Progress 2003, 19 (5), 1403-1409.

Han, M.; Kickhoefer, V. A.; Nemerow, G. R.; Rome, L. H. Targeted Vault Nanoparticles Engineered with an Endosomolytic Peptide Deliver Biomolecules to the Cytoplasm. ACS Nano 2011, 5, 6128-6137.

Heijnen, I. A. F. M.; vanVugt, M. J.; Fanger, N. A.; Graziano, R. F.; deWit, T. P. M.; Hofhuis, F. M. A.; Guyre, P. M.; Capel, P. J. A.; Verbeek, J. S.; vandeWinkel, J. G. J. Antigen Targeting to Myeloid-Specific Human Fc Gamma RI/CD64 Triggers Enhanced Antibody Responses in Transgenic Mice. Journal of Clinical Investigation 1996, 97 (2), 331-338.

Henley, J. P., Sadana, A., 1984. Series-type enzyme deactivations: influence of intermediate activity on deactivation kinetics. Enzyme Microb. Technol. 6 (1), 35-41.

Henley, J. P., Sadana, A., 1985. Categorization of enzyme deactivations using a series-type mechanism. Enzyme Microb. Technol. 7 (2), 50-60.

Hirano, T., Honda, Y., Watanabe, T., Kuwahara, M., 2000. Degradation of bisphenol A by the lignin-degrading enzyme, manganese peroxidase, produced by the white-rot basidiomycete, *Pleurotus ostreatus*. Biosci., Biotechnol., Biochem. 64 (9), 1958-1962.

Ifere, G. O.; He, Q.; Igietseme, J. U.; Ananaba, G. A.; Lyn, D.; Lubitz, W.; Kellar, K. L.; Black, C. M.; Eko, F. O. Immunogenicity and Protection Against Genital *Chlamydia* Infection and Its Complications by a Multisubunit Candidate Vaccine. Journal of Microbiology, Immunology and Infection 2007, 40 (3), 188-200.

Kar, U. K., Srivastava, M. K., Andersson, A., Baratelli, F., Huang, M., Kickhoefer, V. A., Dubinett, S. M., Rome, L. H., Sharma, S., 2011. Novel CCL21-vault nanocapsule intratumoral delivery inhibits lung cancer growth. PLoS One 6 (5), e18758.

Kedersha, N. L.; Heuser, J. E.; Chugani, D. C.; Rome, L. H. Vaults. III. Vault Ribonucleoprotein Particles Open into Flower-Like Structures with Octagonal Symmetry. Journal of Cell Biology 1991, 112, 225-235.

Kedersha, N. L., Rome, L. H., 1986. Isolation and characterization of a novel ribonucleoprotein particle: large structures contain a single species of small RNA. J. Cell Biol. 103 (3), 699-709.

Kelly, K. A.; Robinson, E. A.; Rank, R. G. Initial Route of Antigen Administration Alters the T-Cell Cytokine Profile Produced in Response to the Mouse Pneumonitis Biovar of *Chlamydia trachomatis* following Genital Infection. Infection and Immunity 1996, 64 (12), 4976-83.

Kickhoefer, V. A.; Garcia, Y.; Mikyas, Y.; Johansson, E.; Zhou, J. C.; Raval-Fernandes, S.; Minoofar, P.; Zink, J. I.; Dunn, B.; Stewart, P. L.; Rome, L. H. Engineering of Vault Nanocapsules with Enzymatic and Fluorescent Properties. Proceedings of the National Academy of Sciences of the U.S. Pat. No. 2,005,102, 4348-4352.

Kickhoefer, V. A., Han, M., Raval-Fernandes, S., Poderycki, M. J., Moniz, R. J., Vaccari, D., Silvestry, M., Stewart, P. L., Kelly, K. A., Rome, L. H., 2009. Targeting vault nanoparticles to specific cell surface receptors. ACS Nano 3 (1), 27-36.

Kickhoefer, V. A., Liu, Y., Kong, L. B., Snow, B. E., Stewart, P. L., Harrington, L., Rome, L. H., 2001. The telomerase/vault-associated protein TEP1 is required for vault RNA stability and its association with the vault particle. J. Cell Biol. 152 (1), 157-164.

Kickhoefer, V. A., Searles, R. P., Kedersha, N. L., Garber, M. E., Johnson, D. L., Rome, L. H., 1993. Vault ribonucleoprotein particles from rat and bullfrog contain a related small RNA that is transcribed by RNA polymerase III. J. Biol. Chem. 268 (11), 7868-7873.

Kickhoefer, V. A., Siva, A. C., Kedersha, N. L., Inman, E. M., Ruland, C., Streuli, M., Rome, L. H., 1999a. The 193-kD vault protein, VPARP, is a novel poly(ADP-ribose) polymerase. J. Cell Biol. 146 (5), 917-928.

Kickhoefer, V. A., Stephen, A. G., Harrington, L., Robinson, M. O., Rome, L. H., 1999b. Vaults and telomerase share a common subunit, TEP1. J. Biol. Chem. 274 (46), 32712-32717.

Kong, L. B., Siva, A. C., Rome, L. H., Stewart, P. L., 1999. Structure of the vault, a ubiquitous celular component. Structure 7 (4), 371-379.

Kopeina, G. S., Afonina, Z. A., Gromova, K. V., Shirokov, V. A., Vasiliev, V. D., Spirin, A. S., 2008. Step-wise formation of eukaryotic double-row polyribosomes and circular translation of polysomal mRNA. Nucleic Acids Res. 36 (8), 2476-2488.

Lai, C. Y.; Wiethoff, C. M.; Kickhoefer, V. A.; Rome, L. H.; Nemerow, G. R. Vault nanoparticles containing an adenovirus-derived membrane lytic protein facilitate toxin and gene transfer. ACS Nano 2009, 3 (3), 691-9.

Lai, H. J.; Sethuraman, N.; Stadheim, T. A.; Zha, D. X.; Prinz, B.; Ballew, N.; Bobrowicz, P.; Choi, B. K.; Cook, W. J.; Cukan, M.; Houston-Cummings, N. R.; Davidson, R.; Gong, B.; Hamilton, S. R.; Hoopes, J. P.; Jiang, Y. W.; Kim, N.; Mansfield, R.; Nett, J. H.; Rios, S.; Strawbridge, R.; Wildt, S.; Gerngross, T. U. Optimization of humanized IgGs in glycoengineered *Pichia pastoris*. Nature Biotechnology 2006, 24 (2), 210-215.

Mahendra, S. (2017). Molecular Engineered Enzyme Catalysts for Biodegradation of Water Contaminants. Water Environment and Reuse Foundation Paul L. Busch Award Lecture, Water Environment Federation Technical Exhibition and Conference, Chicago, Ill.

Marcus, L., Ris, H., Halvorson, H., Bretthauer, R., Bock, R., 1967. Occurrence, isolation, and characterization of polyribosomes in yeast. J. Cell Biol. 34 (2), 505-512.

Mikyas, Y.; Makabi, M.; Raval-Fernandes, S.; Harrington, L.; Kickhoefer, V. A.; Rome, L. H.; Stewart, P. L. Cryoelectron Microscopy Imaging of Recombinant and Tissue Derived Vaults: Localization of the MVP N Termini and VPARP. Journal of Molecular Biology 2004, 344 (1), 91-105.

Moore, T.; Ekworomadu, C. O.; Eko, F. O.; MacMillan, L.; Ramey, K.; Ananaba, G. A.; Patrickson, J. W.; Nagappan, P. R.; Lyn, D.; Black, C. M.; Igietseme, J. U. Fc Receptor-Mediated Antibody Regulation of T cell Immunity Against Intracellular Pathogens. Journal of Infectious Diseases 2003, 188 (4), 617-624.

Mrazek, J., Toso, D., Ryazantsev, S., Zhang, X., Zhou, Z. H., Fernandez, B. C., Kickhoefer, V. A., Rome, L. H., 2014. Polyribosomes are molecular 3D nanoprinters that orchestrate the assembly of vault particles. ACS Nano 8 (11), 11552-11559.

Pal, S.; Peterson, E. M.; de la Maza, L. M. Vaccination with the *Chlamydia trachomatis* Major Outer Membrane Protein Can Elicit an Immune Response as Protective as That Resulting from Inoculation with Live Bacteria. Infection and Immunity 2005, 73 (12), 8153-8160.

Rome, L. H.; Kickhoefer, V. A. Development of the Vault Particle as a Platform Technology. ACS Nano 2013, 7 (2), 889-902.

Sharma, S.; Stolina, M.; Luo, J.; Strieter, R. M.; Burdick, M.; Zhu, L. X.; Batra, R. K.; Dubinett, S. M. Secondary Lymphoid Tissue Chemokine Mediates T cell-Dependent Antitumor Responses in vivo. Journal of Immunology 2000, 164 (9), 4558-4563.

Spadaro, J. T., Renganathan, V., 1994. Peroxidase-catalyzed oxidation of azo dyes: mechanism of Disperse Yellow 3 degradation. Arch. Biochem. Biophys. 312 (1), 301-307.

Stephen, A. G., Raval-Fernandes, S., Huynh, T., Torres, M., Kickhoefer, V. A., Rome, L. H., 2001. Assembly of vault-like particles in insect cells expressing only the major vault protein. J. Biol. Chem. 276 (26), 23217-23220.

Sun, J. R.; Coughlin, P.; Salem, H. H.; Bird, P. Production and Characterization of Recombinant Human Proteinase-Inhibitor-6 Expressed in *Pichia-Pastoris*. Biochimica Et Biophysica Acta-Protein Structure and Molecular Enzymology 1995, 1252 (1), 28-34.

Tanaka, H.; Kato, K.; Yamashita, E.; Sumizawa, T.; Zhou, Y.; Yao, M.; Iwasaki, K.; Yoshimura, M.; Tsukihara, T. The Structure of Rat Liver Vault at 3.5 Angstrom Resolution. Science 2009, 323, 384-388.

Tien, M., Kirk, T. K., 1988. Lignin peroxidase of *Phanerochaete chrysosporium*. Methods Enzymol. 161, 238-249.

Wang, J.-H., Hung, W., Tsai, S.-H., 2011. High efficiency transformation by electroporation of *Yarrowia lipolytica*. J. Microbiol. 49, 469-472.

Wang, M., Abad, D., Kickhoefer, V. A., Rome, L. H., Mahendra, S., 2015. Vault nanoparticles packaged with enzymes as an efficient pollutant biodegradation technology. ACS Nano 9 (11), 10931-10940.

Wang, M., Y. Chen, D. Abad, V. A. Kickhoefer, P. Allard, L. H. Rome, and S. Mahendra (2017). Vault Nanoparticles for Water Treatment Applications: Experimental and Educational Approaches. Sixth Sustainable Nanotechnology Organization Conference, Los Angeles, Calif.

Waterham, H. R., Digan, M. E., Koutz, P. J., Lair, S. V., Cregg, J. M., 1997. Isolation of the *Pichia pastoris* glyceraldehyde-3-phosphate dehydrogenase gene and regulation and use of its promoter. Gene 186, 37-44.

Yang, S. C.; Batra, R. K.; Hillinger, S.; Reckamp, K. L.; Strieter, R. M.; Dubinett, S. M.; Sharma, S. Intrapulmonary Administration of CCL21 Gene-Modified Dendritic Cells Reduces Tumor Burden in Spontaneous Murine Bronchoalveolar Cell Carcinoma. Cancer research 2006, 66 (6), 3205-13.

Yang, S. C.; Hillinger, S.; Riedl, K.; Zhang, L.; Zhu, L.; Huang, M.; Atianzar, K.; Kuo, B. Y.; Gardner, B.; Batra, R. K.; Strieter, R. M.; Dubinett, S. M.; Sharma, S. Intratumoral Administration of Dendritic Cells Overexpressing CCL21 Generates Systemic Antitumor Responses and Confers Tumor Immunity. Clinical Cancer Research 2004, 10 (8), 2891-901.

All scientific and technical terms used in this application have meanings commonly used in the art unless otherwise specified.

As used herein, the terms "subject", "patient", and "individual" are used interchangeably to refer to humans and non-human animals. The term "non-human animal" includes all vertebrates, e.g., mammals and non-mammals, such as non-human primates, horses, sheep, dogs, cows, pigs, chickens, and other veterinary subjects and test animals. In some embodiments of the present invention, the subject is a mammal. In some embodiments of the present invention, the subject is a human.

The use of the singular can include the plural unless specifically stated otherwise. As used in the specification and the appended claims, the singular forms "a", "an", and "the" can include plural referents unless the context clearly dictates otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

The phrase "comprises, consists essentially of, or consists of" is used as a tool to avoid excess page and translation fees and means that in some embodiments the given thing at issue comprises something, and in some embodiments the given thing at issue consists of something. For example, the sentence "In some embodiments, the composition comprises, consists essentially of, or consists of A" is to be interpreted as if written as the following two separate sentences: "In some embodiments, the composition comprises A. In some embodiments, the composition consists essentially of A. In some embodiments, the composition consists of A." Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C."

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A yeast host cell, which comprises a nucleic acid sequence that encodes a major vault protein (MVP) sequence having 95-100% sequence identity to SEQ ID NO: 2, wherein said nucleic acid sequence comprises at least 95% sequence identity to SEQ ID NO: 1.

2. The yeast host cell according to claim 1, wherein the yeast host cell contains multiple copies of the nucleic acid sequence.

3. The yeast host cell according to claim 1, wherein the nucleic acid sequence is under the control of a promoter such as a constitutive promoter, an inducible promoter, or a yeast promoter.

4. The yeast host cell according to claim 1, wherein the yeast host cell has been recombinantly modified to express one or more passenger peptides.

5. The yeast host cell according to claim 1, wherein the yeast host cell is a microorganism belonging to the family Saccharomycetaceae.

6. A method of making a major vault protein (MVP) in a yeast host, which comprises culturing the yeast host cell according to claim 1 under conditions suitable for expression of the major vault protein.

7. A method of making a vault particle in a yeast host, which comprises culturing the yeast host cell according to claim 1 under conditions suitable for formation of the vault particle.

8. A method of producing a commercial-scale amount of vault particles, which comprises culturing the yeast host cell according to claim 1 in a cell culture medium to obtain a host cell culture that is at or near a stationary growth phase.

9. The method according to claim 7, and further comprising extracting the vault particle from the yeast host cell or cells of the host cell culture.

10. The method according to claim 7, and further comprising packaging one or more passenger molecules on or in the vault particle by (a) covalently linking the one or more passenger molecules to the N-terminus and/or C-terminus of the major vault protein, (b) mINT fusion packaging, and/or (c) passive packaging.

11. The method according to claim 7, and further comprising packaging one or more mINT passenger molecules within the cavity of the vault particle.

12. A composition comprising one or more yeast host cells according to claim 1, one or more major vault proteins made by culturing the one or more yeast host cells, and/or one or more vault particles expressed by the one or more yeast host cells.

13. The method according to claim 8, and further comprising extracting the vault particle from the yeast host cell or cells of the host cell culture.

14. The method according to claim 8, and further comprising packaging one or more passenger molecules on or in the vault particle by (a) covalently linking the one or more passenger molecules to the N-terminus and/or C-terminus of the major vault protein, (b) mINT fusion packaging, and/or (c) passive packaging.

15. The yeast host cell according to claim 1, wherein the yeast host cell is a microorganism belonging to the genus *Pichia*.

16. The yeast host cell according to claim 1, wherein the amino acid sequence of the major vault protein is SEQ ID NO: 2.

17. A yeast host cell comprising a nucleic acid sequence comprising SEQ ID NO: 1.

18. The yeast host cell according to claim 1, wherein said nucleic acid comprises at least 96% sequence identity to SEQ ID NO: 1.

19. The yeast host cell according to claim 1, wherein said nucleic acid comprises at least 97% sequence identity to SEQ ID NO: 1.

20. The yeast host cell according to claim 1, wherein said nucleic acid comprises at least 98% sequence identity to SEQ ID NO: 1.

21. The yeast host cell according to claim 1, wherein said nucleic acid comprises at least 99% sequence identity to SEQ ID NO: 1.

* * * * *